(12) United States Patent
Golovchenko et al.

(10) Patent No.: US 6,783,643 B2
(45) Date of Patent: Aug. 31, 2004

(54) CONTROL OF SOLID STATE DIMENSIONAL FEATURES

(75) Inventors: Jene A. Golovchenko, Lexington, MA (US); Daniel Branton, Lexington, MA (US); Michael J. Aziz, Concord, MA (US); Jiali Li, Fayetteville, AR (US); Derek M. Stein, Somerville, MA (US); Ciaran J. McMullan, Magherafelt (IE)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/186,105

(22) Filed: Jun. 27, 2002

(65) Prior Publication Data

US 2003/0066749 A1 Apr. 10, 2003

Related U.S. Application Data

(63) Continuation-in-part of application No. 09/599,137, filed on Jun. 22, 2000, now Pat. No. 6,464,842.
(60) Provisional application No. 60/140,021, filed on Jun. 22, 1999, and provisional application No. 60/301,400, filed on Jun. 27, 2001.

(51) Int. Cl.[7] .............................................. C23C 14/34
(52) U.S. Cl. .............................. 204/192.3; 204/192.32; 204/192.33; 204/192.34
(58) Field of Search ........................ 204/192.3, 192.32, 204/192.33, 192.34, 192.11

(56) References Cited

U.S. PATENT DOCUMENTS

| 4,455,192 A | 6/1984 | Tamai ......................... 156/628 |
| 4,728,591 A | 3/1988 | Clark et al. ..................... 430/5 |
| 4,855,197 A | 8/1989 | Zapka et al. .................... 430/5 |
| 5,244,527 A | 9/1993 | Aoyagi ......................... 156/345 |
| 5,319,197 A | 6/1994 | Friedhelm .................... 250/305 |

(List continued on next page.)

FOREIGN PATENT DOCUMENTS

| DE | 44 33 845 A | 3/1996 |
| EP | 0 632 494 A | 1/1995 |
| WO | WO-00 78668 A | 12/2000 |

OTHER PUBLICATIONS

Erlebacher et al., "Spontaneous Pattern Formation on Ion Bombarded Si(001)", Phys. Rev. Let., vol. 82, No. 11, Mar. 15, 1999, pp. 2330–2333.*

(List continued on next page.)

Primary Examiner—Steven Versteeg
(74) Attorney, Agent, or Firm—Theresa A. Lober

(57) ABSTRACT

A solid state structure having a surface is provided and exposed to a flux, F, of incident ions under conditions that are selected based on:

$$\frac{\partial}{\partial t}C(r, t) = FY_1 + D\nabla^2 C - \frac{C}{\tau_{trap}} - FC\sigma_C,$$

where C is concentration of mobile adatoms at structure surface, r is vector surface position, t is time, $T_1$ is number of adatoms created per incident ion, D is adatom diffusivity, $\tau_{trap}$ is average lifetime of an adatom before adatom annihilation occurs at a structure surface defect characteristic of structure material, and $\sigma_C$ is cross-section for adatom annihilation by incident ions characteristic of selected ion exposure conditions. Ion exposure condition selection controls sputtering of the structure surface by incident ions to transport, within the structure including the structure surface, structure material to a feature location, in response to the ion flux exposure, to produce a feature substantially by locally adding structure material to the feature location.

22 Claims, 21 Drawing Sheets

U.S. PATENT DOCUMENTS

| | | | |
|---|---|---|---|
| 5,420,067 A | 5/1995 | Hsu | 437/180 |
| 5,486,264 A | 1/1996 | Ghandour | 156/635.1 |
| 5,556,462 A | 9/1996 | Celii et al. | 177/85 |
| 5,753,014 A | 5/1998 | Van Rijn | 96/12 |
| 5,780,852 A | 7/1998 | Shu | 250/304 |
| 5,789,024 A | 8/1998 | Levy et al. | 427/244 |
| 5,798,042 A | 8/1998 | Chu et al. | 210/490 |
| 5,851,842 A | 12/1998 | Katsumata et al. | 438/9 |
| 5,868,947 A | 2/1999 | Sakaguchi et al. | 216/2 |
| 5,876,880 A | 3/1999 | Vonach et al. | 430/5 |
| 5,893,974 A | 4/1999 | Keller et al. | 210/483 |
| 5,962,081 A | 10/1999 | Ohman et al. | 427/534 |
| 6,106,677 A | 8/2000 | Sandhu | 204/192.3 |
| 6,464,842 B1 * | 10/2002 | Golovchenko et al. | 204/192.13 |

OTHER PUBLICATIONS

Gribov et al., "A new fabrication process for metallic point contacts", Microelect. Eng., vol. 35, pp. 317–320 (1997).*

Yoldas et al., "Formation of Broad Band Antireflective Coatings on Fused Silica for High Power Laser Applications," Thin Solid Films, vol. 129, pp. 1–14, 1985.

Shank et al., "Fabrication of high aspect ratio structures for microchannel plates," J. Vac. Sci. Technol. B. vol. 13, No. 6, pp. 2736–2740, Nov./Dec. 1995.

Gribov et al., "A new fabrication process for metallic point contacts," Microelectronic Engineering, vol. 35, pp. 317–320, 1997.

Erlebacher et al., Spontaneous Pattern Formation on Ion Bombarded Si(001), Phys. Rev. Letts., vol. 82, No. 11, pp. 2330–2332, Mar. 1999.

Deshmukh et al., "Nanofabrication using a stencil mask," Appl. Phys. Letts. vol. 75, No. 11, pp. 1631–1633, Sep. 1999.

Wellock et al., "Giant magnetoresistance of magnetic multilayer point contacts," Phys. Rev. B, vol. 60, No. 14, pp. 10291–10301, Oct. 1999–II.

Desai et al., "Characterization of micromachined silicon membranes for immunoisolation and bioseparation applications," Jnl. of Membrane Science, vol. 159, pp. 221–231, 1999.

Erlebacher et al., Nonlinear amplitude evolution during spontaneous patterning of ion–bombarded.Si(001), J. Vac. Sci. Technol. A, vol. 18, No. 1 pp. 115–120, Jan./Feb. 2000.

Li et al., "Ion–beam sculpting at nanometre length scales," Nature, vol. 412, pp. 166–169, Jul. 2001.

* cited by examiner

Closing Trenches

3 KeV, 20°C    3 KeV, 20°C

Opening Trenches

3 KeV, -100°C    3 KeV, -100°C

CONTROL OF SOLID STATE DIMENSIONAL FEATURES

This application claims the benefit of U.S. Provisional Application No. 60/301,400, filed Jun. 27, 2001, the entirety of which is hereby incorporated by reference. This application is a continuation in part of co-pending U.S. Nonprovisional application Ser. No. 09/599,137, filed Jun. 22, 2000, now U.S. Pat. No. 6,464,842, which claims the benefit of U.S. Provisional Application No. 60/140,021, filed Jun. 22, 1999, the entirety of which is hereby incorporated by reference.

CROSS REFERENCE TO RELATED APPLICATION

This application is related to co-pending U.S. Nonprovisional application Ser. No. 09/602,650, entitled "Molecular and Atomic Scale Evaluation of Biopolymers," filed Jun. 22, 2000, and hereby incorporated by reference in its entirety.

STATEMENT REGARDING FEDERALLY SPONSORED RESEARCH

This invention was made with Government support under Contract No. N65236-98-1-5407, and Contract No. F49620-01-1-0467, both awarded by DARPA; under Contract No. DMR-0073590, awarded by NSF; under Contract No. DE-FG02-89ER45401, and Contract No. DE-FG02-01ER45922, both awarded by DOE; and under Contract No. N00014-01-1-0788, awarded by ONR. The Government has certain rights in the invention.

BACKGROUND OF THE INVENTION

This invention relates to fabrication of solid state structures, and more particularly relates to dimensional control of solid state structural features.

Precise dimensional control of solid state structural features is essential for many applications in fields ranging from biology and chemistry to physics, optics, and microelectronics. The term "solid state" is here meant to refer to non-biological materials generally. Frequently the successful fabrication of a solid state system critically depends on an ability to articulate specific structural features, often of miniature dimensions, within very tight tolerances. Accordingly, as solid state systems evolve to the micro-regime and further to the nano-regime, nanometric dimensional feature control is increasingly a primary concern for system feasibility.

There have been established a wide range of microfabrication techniques for producing and controlling structural feature dimensions in micromechanical and microelectromechanical systems. For example, high resolution lithographic techniques and high-precision additive and subtractive material processing techniques have been proposed to enable small-scale feature fabrication. But in the fabrication of many nano-regime systems, in which structural feature dimensions of a few nanometers are of importance, it is generally found that conventionally-proposed techniques often cannot form the requisite nano-scale features reproducibly or predictably, and often cannot be controlled on a time scale commensurate with production of such nano-scale features. As a result, volume manufacture of many systems that include nanometric feature dimensions and/or tolerances is not practical or economical.

SUMMARY OF THE INVENTION

The invention provides processes and corresponding process control methodology that enable reproducible and predictable production of structural features for solid state mechanical and electromechanical systems. The processes of the invention can be controlled to produce, control, and/or change feature dimensions in the nano-regime and can include real time feedback control operating on a time scale commensurate with the formation of nano-scale solid state features.

In one technique provided by the invention, for fabricating a feature of a solid state structure, a solid state structure having a surface is provided and is exposed to a flux, F, of incident ions. The conditions of this incident ion exposure are selected based on:

$$\frac{\partial}{\partial t}C(r,t) = FY_1 + D\nabla^2 C - \frac{C}{\tau_{trap}} - FC\sigma_C,$$

where C is the concentration of mobile adatoms at the structure surface, r is vector surface position, t is time, $Y_1$ is the number of surface adatoms created per incident ion, D is the surface adatom diffusivity, $\tau_{trap}$ is the average lifetime of a surface adatom before adatom annihilation occurs at a structure surface defect characteristic of material of the solid state structure, and $\sigma_C$ is a cross-section for surface adatom annihilation by incident ions that is characteristic of the selected ion exposure conditions.

The selected ion exposure conditions control sputtering of the structure surface by the incident ions and result in transport, within the structure including the structure surface, of material of the structure to a selected feature location, in response to the ion flux exposure. This produces the desired feature substantially by locally adding material of the structure to the feature location. This technique can be employed for changing a dimension of, rather than, or in addition to, fabricating a feature at a selected feature location.

"Solid-state" is used herein to refer to materials that are not of biological origin. By biological origin is meant naturally occurring, i.e., isolated from a biological environment such as an organism or cell, or otherwise occurring in nature, or a synthetically manufactured version of a biologically available structure, or a synthetic or non-naturally occurring homologue or derivative of a naturally occurring material that substantially retains the desired biological traits of interest. Solid-state encompasses both organic and inorganic materials. The structure can be provided as, e.g., a substrate of inorganic or material, or crystalline material, and can be provided as a semiconductor wafer, a membrane, a layer in which the prespecified feature is to be fabricated, or other suitable structure.

The incident ion flux exposure condition selection can include, e.g., selection of structural material composition, temperature, electronic charge state, electronic doping, and surface defect characteristics, selection of ion flux, energy, species, or time structure, selection of ambient gas species and/or pressure, or selection of the value of another process parameter of the exposure.

The ion exposure conditions can also be selected by carrying out at least one test incident ion exposure of the solid state structure material under selected test incident ion exposure conditions. A physical detection species is directed toward a designated structure location during each test incident ion exposure. Then the detection species is detected in a trajectory from the designated structure location to indicate feature fabrication dependence on the test ion exposure conditions. The ion exposure conditions can then be selected based on the test ion exposure conditions and the corresponding indicated feature fabrication dependence on the test ion exposure conditions.

These processes enable fabrication of a wide range of structural features in a manner that is reproducible, controllable, and efficient. Applications in fields ranging from biology to microelectronics are enabled by these processes, and can be carried out in a manner that is commercially viable. Other features and advantages of the invention will be apparent from the following description and accompanying drawings, and from the claims.

DETAILED DESCRIPTION OF THE INVENTION

Figure 1A:
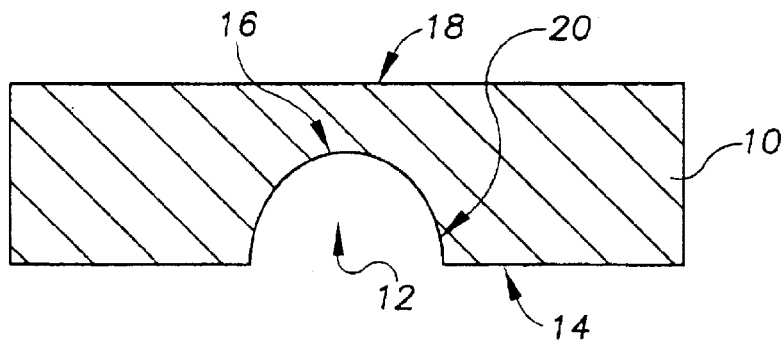
FIGS. 1A–1D are schematic cross-sectional views of fabrication sequence steps for the production of an aperture in accordance with the invention.

The processes for dimensional feature control provided by the invention can be directed to a wide range of materials and structural configurations. The example processes here described are meant to be illustrative but not to represent specific limitations in materials or configurations. The processes of the invention are particularly well-suited for precisely controlling structural feature dimensions, and for enabling such control on the scale of nanometers. This control can be especially advantageous for the precise formation and definition of nanometric-sized features and spaces, such as gaps existing as an aperture, e.g., pores, slits, orifices, vents, and holes, as well as trenches, channels, troughs, and in general, the spacing between two or more distinct feature edges.

Referring to FIG. 1, in one example implementation of a method provided by the invention for precisely and reproducibly defining the spacing of features, there is carried out a process for forming an aperture of a prespecified extent, e.g., diameter, in a structural layer. In a first process step, referring to FIG. 1A, a starting structure 10 is provided, shown in cross-section in the figure. Such starting structure 10 can be supplied as, e.g., a substrate, a thick or thin layer provided on a support such as a substrate, a membrane, or suitable structure. A cavity 12 is formed in the structure 10 on a selected surface 14 of the structure and in a region at which an aperture is desired.

The cavity 12 extends into the bulk of the structure 10 for only a fraction of the structure's thickness, rather than through the entire thickness of the structure, to an opposing surface 18. As a result, the deepest level, i.e., the bottom 16, of the formed cavity lies at some midpoint in the structure's bulk. As explained in more detail below, the geometry of the cavity bottom 16 and the cavity sidewalls 20 are preferably selected to enable controlled formation of a limiting aperture of controlled transverse and longitudinal dimensions in later processing steps. In the example illustrated, a bowl-shaped cavity is employed.

Figure 1B:
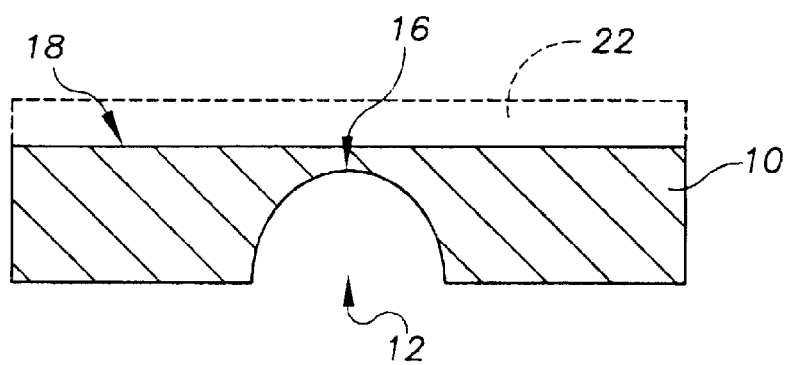
Figure 1C:
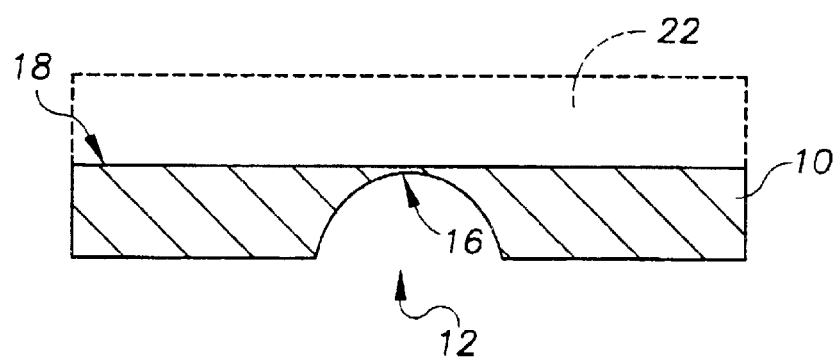

Referring to FIGS. 1B and 1C, once the cavity is produced, the structure is progressively thinned from the cavity-free surface 18. As the thinning is continued, a portion 22 of the structure is increasingly removed, shown by dotted lines. This causes the cavity-free surface 18 of the structure to advance toward the bottom 16 of the cavity.

Figure 1D:
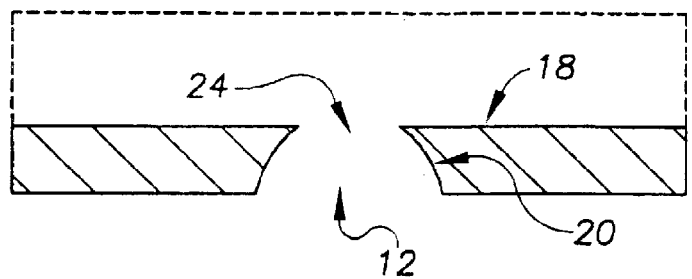

Continued thinning of the structure results in the intersection of the cavity-free surface 18 with the bottom 16 of the cavity, as shown in FIG. 1D. When this intersection occurs, a limiting aperture 24 is formed which transforms the cavity 12 to an aperture extending through the thickness of the structure. Further thinning of the structure causes the cavity-free surface 18 to intersect upper sidewall locations of the cavity, whereby the limiting aperture 24 takes on that profile of the sidewalls which exists at a given cavity intersection depth. In the example illustrated, the diameter of the limiting aperture 24 increases as thinning is continued, given the bowl shape of the cavity. It is to be recognized, however, that the diameter of the limiting aperture can be made to decrease as thinning is continued, for a corresponding cavity sidewall profile. In addition, asperities or other distinct profile features or geometry can be provided along the cavity sidewalls for controlling limiting aperture geometry.

This aperture forming process provides distinct advantages in that it does not rely on direct lithographic techniques for defining final limiting aperture and wall dimensions. As a result, the aperture forming process is not constrained by lithographic resolution limits. The process enables production of a limiting aperture dimension or diameter as small as 1–2 nanometers or less without the need for exotic or expensive processing apparatus.

As explained above, this aperture formation process can be carried out on any of a wide range of structures, such as substrates, layers, and films provided on a supporting structure or free-standing as, e.g., membranes. Solid state materials in general can be employed as the structural material in which an aperture is formed; microelectronic or semiconductor materials can be particularly effective in enabling efficient processing techniques, as described below. For example, the broad classes of inorganic and organic glassy materials, such as oxides, glasses, plastics, polymers, and organic films, e.g., PMMA, as well as crystalline materials, such as semiconductors, e.g., silicon and silicon nitride, and metals, as well as other materials can be employed. The invention is not limited to a particular structural material or class of structural materials. Preferably, the structural material is selected to meet the criteria of the application specified for the aperture.

The method is particularly well-suited for enabling formation of apertures in membranes, and for providing the nano-regime control of aperture formation that is required for many membrane applications. In the formation of a membrane aperture, microelectronic and semiconductor materials and fabrication processes can be advantageously exploited in accordance with the invention to enable cost-effective and efficient manufacturability.

Figure 2A:
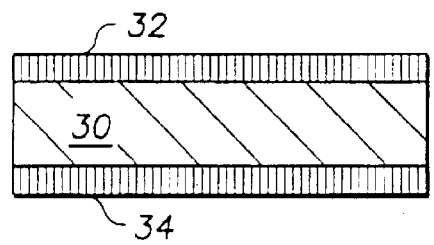
FIGS. 2A–2G are schematic cross-sectional views of an example fabrication sequence of steps for the production of the cavity of FIG. 1A in a membrane.

Referring to FIG. 2, in an example microfabrication process provided by the invention for forming an aperture in a membrane, a starting substrate 30, e.g., a silicon wafer, is provided, as shown in FIG. 2A. A selected membrane material, e.g., silicon nitride, is provided as a coating layer 32, 34 on the upper and lower surfaces, respectively, of the wafer. The thickness of the coating layer 34 is that thickness selected for the membrane to be formed. In one example, a silicon-rich, low-stress, silicon nitride layer of about 50 nm in thickness is deposited on the silicon wafer by conventional chemical vapor deposition (CVD) processing. It is recognized that additional membrane materials, e.g., silicon dioxide, can be deposited before or after deposition of the silicon nitride layers for mechanical stress control or other consideration. The silicon nitride layer can also be further processed, e.g., by ion implantation, to control mechanical membrane stress or adjust electrical or thermal conductivity of the membrane as desired for a given application.

Figure 2B:
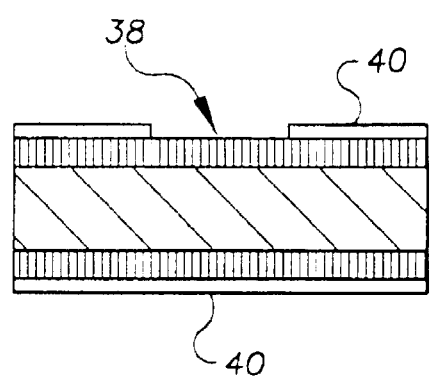
Figure 2C:
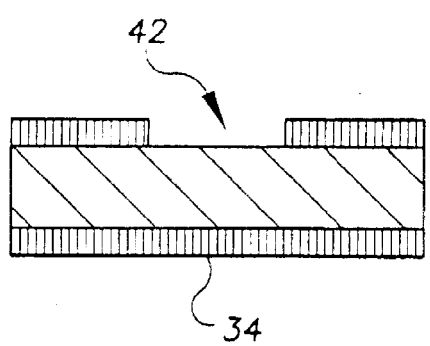

As shown in FIG. 2B, a layer of photoresist 40 is formed on one of the deposited nitride layers and patterned to define a nitride etch window 38. The opposing surface of the wafer is blanket coated with a photoresist layer 40. Then, as shown in FIG. 2C, the silicon nitride exposed by the nitride etch window 38 is removed by, e.g., conventional reactive ion etching techniques. This exposes a substrate etch window 42. The opposing nitride layer 34 is protected from this etch by the blanket photoresist layer 40, which is removed at the etch completion.

Figure 2D:
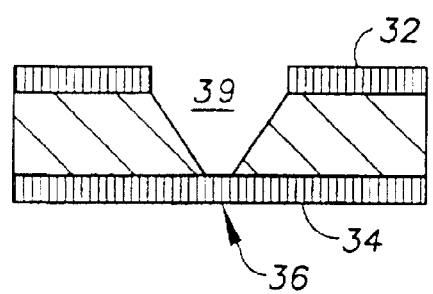

Next, referring to FIG. 2D, the silicon wafer is bulk micromachined by a suitable etch procedure, e.g., a conventional anisotropic wet etch process employing KOH. Preferably, the bulk wafer etch process employed is characterized by a high selectivity to the wafer material over the membrane material. In the example illustrated, the KOH etch substantially does not attack the silicon nitride layers. Continuation of the etch through the thickness of the wafer thereby produces a self-supporting nitride membrane 36 in a nitride layer 34. The nitride membrane forms the bottom of a pyramidal well 39 etched out of the silicon wafer due to the anisotropic, crystallographic-specific nature of the KOH etch. The extent of the nitride membrane is thus determined by the thickness and crystallographic orientation of the starting silicon wafer. As will be recognized, the membrane dimensions can therefore be controlled as-desired.

Figure 2E:
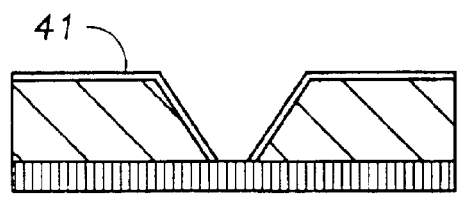

Referring to FIGS. 2D–2E, the remaining layer 32 of silicon nitride opposite the membrane layer can then removed if desired by, e.g., conventional reactive ion etching, and then a layer of silicon dioxide 41 is optionally grown on the exposed silicon surfaces, if electrical insulation of the silicon wafer is desired for a given application. Conventional wet or thermal oxide growth can be preferred over a CVD oxide layer such that oxide is only formed on the silicon surfaces in the manner illustrated. If, however, a composite membrane is desired, e.g., for mechanical stress control, then a CVD or other deposition process can be employed to produce an oxide layer on both the silicon wafer and the lower silicon nitride membrane surfaces, or on the nitride membrane surface alone.

Figure 2F:
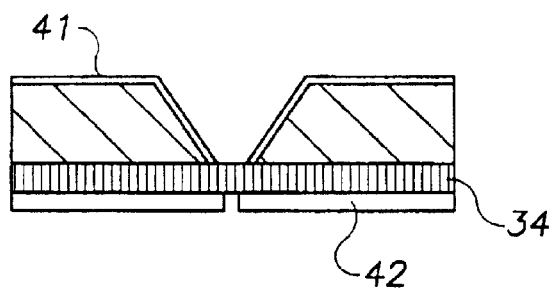

In a next step of the process, referring to FIG. 2F and referring back to FIG. 1A, a cavity is formed in a selected surface of the membrane. In one example cavity formation process, an etching process, as illustrated, a layer of resist 42 is formed on the lower membrane surface, i.e., the membrane surface opposite that in the pyramidal wafer well. The resist is then patterned to define the cavity to be formed in the membrane. This choice of surface for the cavity can be preferable for enabling a selected lithography technique on a flat surface; it can be difficult to effectively pattern a layer of photoresist provided on the membrane surface at the bottom of the silicon pyramidal well. If desired for a given application, however, the cavity can be formed on such a surface with lithographic techniques specific to such a configuration. The invention contemplates the use of photolithography, electron beam lithography, and other suitable lithographic processes for defining the cavity pattern. It is to be recognized that the selected lithographic process is preferably suited to the dimensions of the cavity; e.g., electron beam lithography can be preferred over conventional photolithography for cavities having submicron dimensions.

Figure 2G:
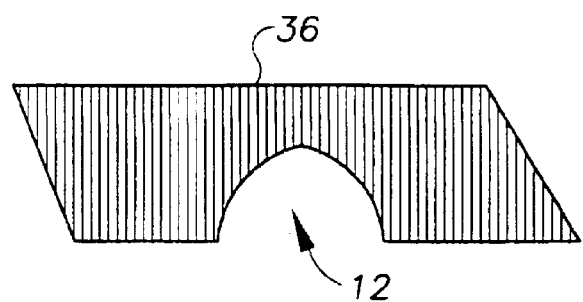

As explained above, the sidewall profile of the cavity to be formed in the membrane can be specified to produce a selected limiting aperture geometry. The lithographic step defining the cavity, as well as the nature of the cavity etch process itself, can also be employed to define the cavity sidewall profile. In one example scenario, the selected lithographic cavity pattern is continuous, e.g., as a circle, and a relatively isotropic etch process, e.g., an isotropic reactive ion etch process, is carried out to form a bowl-shaped cavity 12 in the nitride membrane 36, as shown in FIG. 2G. An isotropic reactive ion etch process inherently forms the bowl shape extending from a circular photolithographic pattern.

The invention contemplates the use of substantially any cavity pattern for achieving a desired cavity geometry. Square, rectangle, hexagonal, or other pattern, symmetric or asymmetric, can be employed. Due to the batch nature of lithographic processes and other microfabrication processes employed in the aperture forming method, arrays of cavities, of varying extent and geometry, can be defined in a single structure such as the membrane illustrated. Because the aperture formation process of the invention relies on structural thinning, rather than lithography, to define the final limiting aperture geometry, the largest lateral dimension of the cavity can be much greater than the desired limiting aperture extent; in general, the largest cavity pattern dimension can be two or more orders of magnitude larger than a selected limiting aperture diameter. Preferably, given the characteristics of a selected cavity etch process, the cavity pattern extent is correspondingly selected to produce a desired extent at the cavity bottom, and to produce a range of cavity expanses between the cavity bottom and the material surface.

Any suitable cavity etch process can be employed, including, e.g., plasma etching, focused reactive ion etching, focused ion beam etching, wet chemical etching, or other selected technique. Whatever etch process is selected, it is to be controlled to enable termination of the etch at a cavity bottom located at some distance within the membrane thickness or other structure in which the cavity is formed, i.e., at a point between the surfaces of the structure. For etch processes that are fully characterized for the structural material being employed, this can be accomplished by a timed etch; conventional diagnostic techniques otherwise can be employed in the conventional manner to produce a cavity bottom at a selected location in a membrane other structure. It is not required in accordance with the invention to precisely position the cavity bottom at a known, a priori depth in the structure. The progressive structural thinning process of the invention is particularly advantageous in this regard; no precise control or knowledge of the depth of the cavity is required to precisely produce an aperture. In addition, a combination of etch processes can be employed as-necessary for cavity formation in a given material or composite of materials. For example, where a composite membrane is formed of silicon nitride and silicon dioxide layers, the chemistry of a selected cavity etch, such as a plasma etch, can be adjusted over the course of the etch based on the material to be etched at a given time in formation of the cavity. Similarly, a combination of etch processes can be employed to alter the cavity sidewall profile as a function of cavity depth. For example, a combination of isotropic and anisotropic wet etches can be employed to produce selected curvature and slant of cavity sidewalls formed in a nitride or silicon layer or membrane. A combination etch such as this enables the formation of asperities or other distinct features to be located at the limiting aperture.

Referring back to FIGS. 1B–1D, once a cavity has been formed in the selected membrane or other structure, thinning of the structure is then carried out on the structure surface opposite that in which the cavity was formed, employing an appropriate procedure to open a limiting aperture in the structure. The invention contemplates a wide range of thinning processes and is not limited to a particular thinning technique; all that is required is the ability to etch back the structure from a surface opposing that in which the cavity was formed.

For many applications, a particularly well-suited thinning process is ion beam sputtering. In such a process, a beam of ions is directed to the structure surface to be thinned to sputter etch away material from that surface. In typical ion beam sputtering processes at relatively low beam energies, e.g., in the range of keV, for every incident ion, on average, a single atom of material is ejected from the sputtering target; sputtering may thus be considered as an atomic-scale version of "sand blasting." In the case of, e.g., a silicon nitride membrane, such sputter etching results in the removal of about one atomic layer of silicon nitride from the membrane per second for incident ion fluxes between about $10^{14}$–$10^{15}$ ions/cm$^2$/sec. When the surface exposed to the sputtering beam has been sufficiently thinned that the surface intersects with the cavity bottom, a limiting aperture is formed.

The invention contemplates a wide range of additional thinning processes, including ion beam assisted etching, ion beam induced etching, electron beam etching or assisted etching, plasma and reactive ion etching, wet etching such as electrochemical etching, chemomechanical polishing, and other fabrication and manufacturing processes that enable controlled thinning of a structure to intersect a cavity on a surface opposite that being thinned. These aperture formation processes can be advantageous for many applications because during the thinning etch, the etch species, e.g., a sputtering ion beam or reactive plasma environment, need not be focused on a particular location of the structure surface being thinned. A blanket exposure of the structure surface can be employed to thin the entire extent of the structure. All that is required is that the structure surface including the cavity be isolated, i.e., shielded, from the etch species attacking the opposing surface. This results in nano-regime precision in feature formation without the requirement of nano-regime control of the etch apparatus and species.

Whatever thinning process is selected, the inventors herein have discovered that highly precise aperture formation can be accomplished by implementing a feedback mechanism during the thinning process. This feedback mechanism is based on detection of a physical species provided during the thinning etch in a manner that is indicative of the physical dimensions of a feature, e.g., an aperture, that is being produced by the etch. Such feedback enables real time control of the aperture formation process, whereby a precise and prespecified aperture diameter can be reliably and reproducibly formed. As explained later in the description, this feedback mechanism can in general enable precise sculpting of nanometric features and nanostructures, and finds wide application for micro- and nano-systems.

Considering feedback control in the aperture formation process of the invention more specifically, when an etch species, such as a beam of sputtering ions, thins a structure to the point that an aperture is formed, ions from the beam are at that point in time enabled to pass through the aperture. Thereafter, the number of ions passing through the aperture per unit time is proportionally related to the increasing diameter of the aperture as the thinning etch continues. Detection and quantification, e.g., by counting, of the rate and/or number of ions passing through the aperture thereby is indicative of the aperture diameter at any given time during the etch.

As a result, a selected aperture diameter can be prespecified based on a rate and/or number of ions expected to pass through the aperture before the selected diameter is produced. During a thinning etch process, a first passage of ions through a newly-formed limiting aperture can be detected, and the number of ions passing through the aperture as its limiting aperture dimension enlarges can be individually detected and quantified. When the prescribed number of ions pass through the aperture, a controlling signal can be sent to the sputtering ion beam controller to terminate the etch process at the desired aperture dimension. In addition, it is recognized in accordance with the invention that detection of a physical species can be carried even prior to the time at which an aperture is formed. For example, the level of X-rays produced by the ion beam gun that are detected as passing through the structure being thinned can be expected to increase as the thickness of the structure decreases. Detection of ions similarly can be made even prior to aperture opening. This enables control of the process even prior to the final opening of the aperture.

Figure 3A:
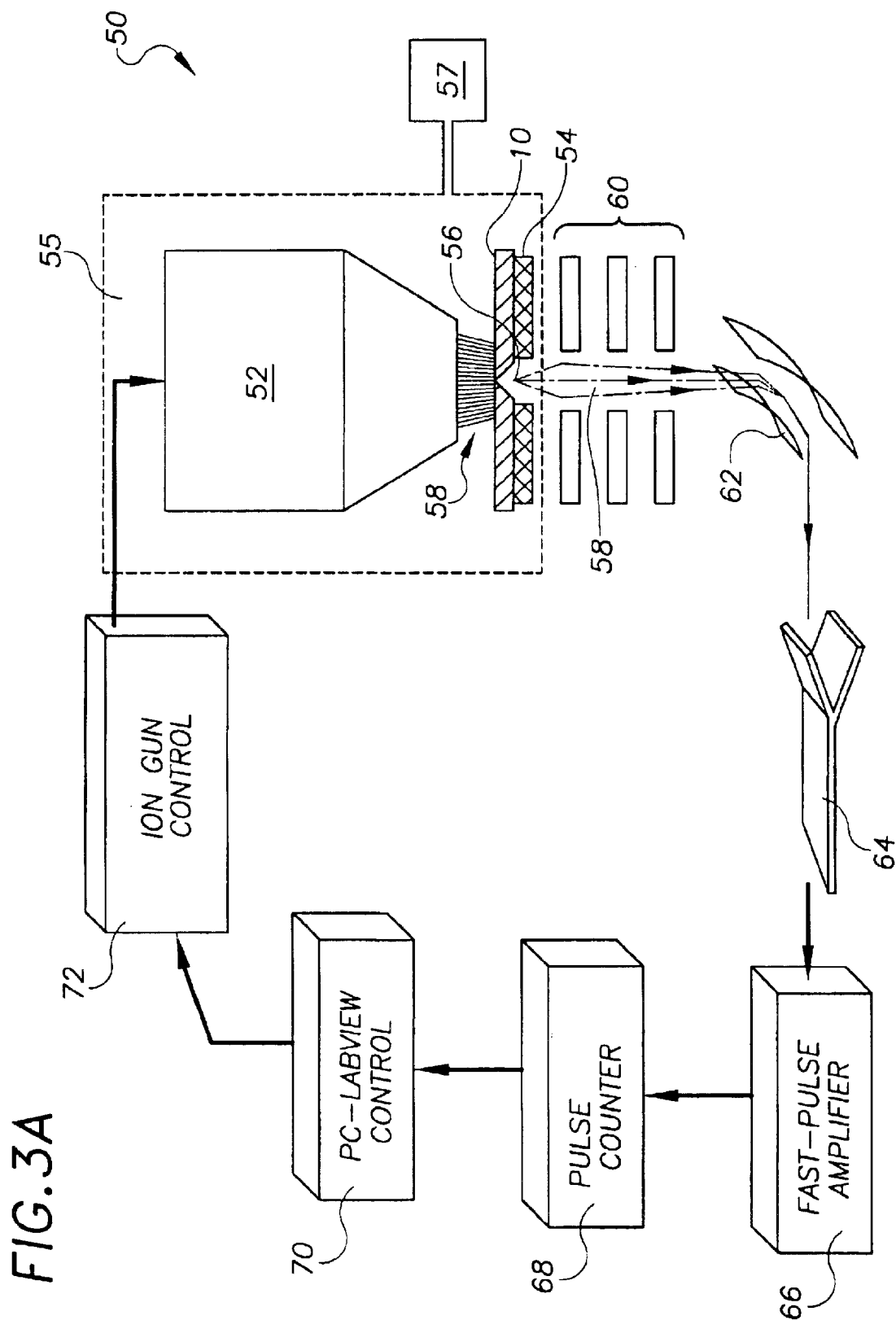
FIGS. 3A–3B are schematic diagrams of an ion beam sputtering system configured in accordance with the invention to implement precision feedback control.
Figure 3B:
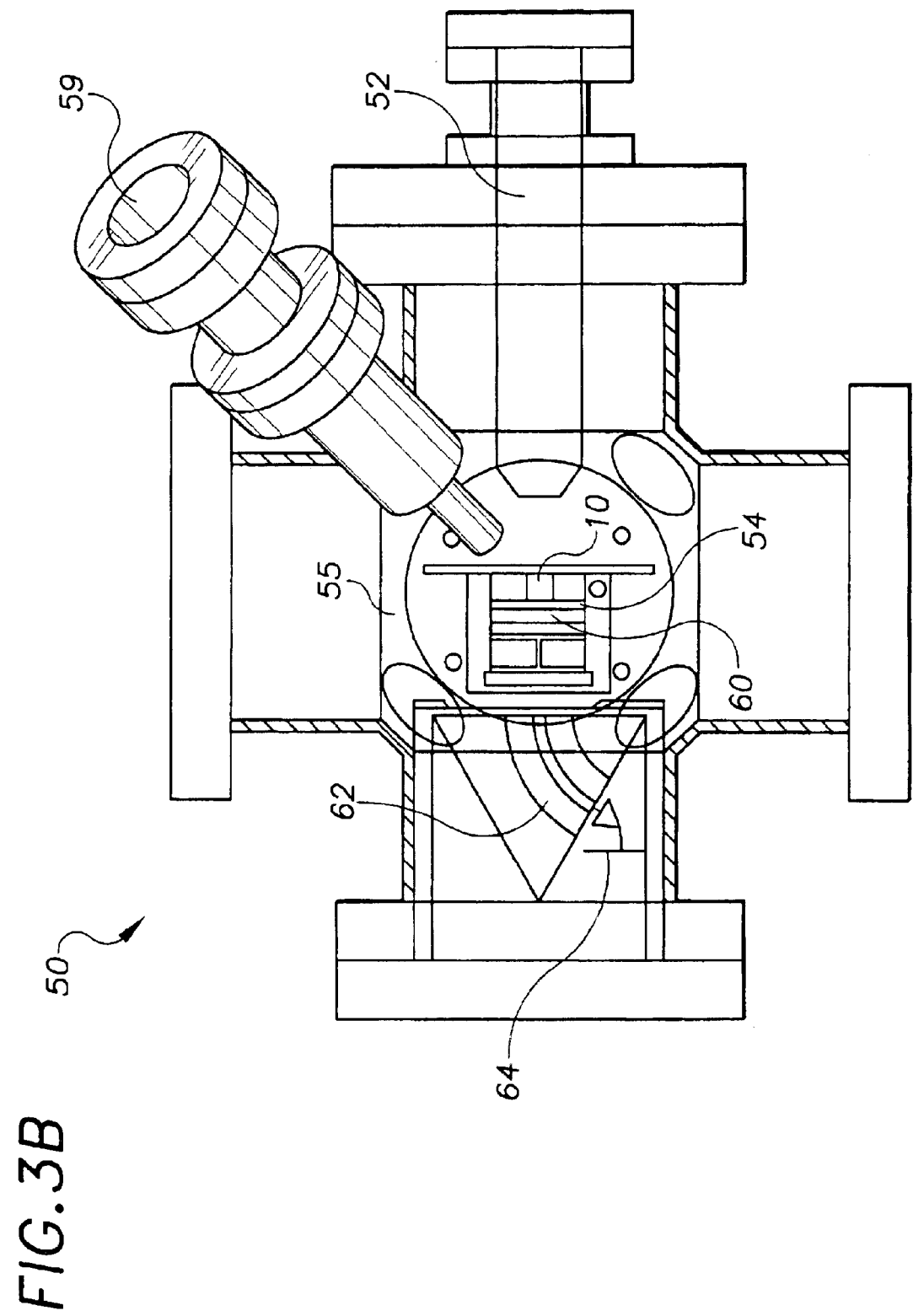

Referring to FIGS. 3A–3B there is schematically shown a system 50 for implementing this feedback-controlled sputtering process. The system includes an ion gun 52, e.g., an ion gun capable of producing an ion beam with an energy range and diameter suitable for a given application. In general, an energy between about 1 eV and about several hundred KeV and a beam diameter between about a few nanometers to spatially very broad beams can be employed. A vacuum etch chamber 55 is provided in which the etch process can be carried out. Preferably, the etch chamber pressure is well-controlled such that etch environment pressures of less than about $10^{-8}$ Torr can be maintained during the etch process. A turbomolecular pump 57 is provided for pressure control and maintenance. Optionally, a mass spectrometer can be provided for monitor and analysis of the etch environment species.

A structure holder 54 is provided for supporting a structure 10 in which an aperture is to be formed, e.g., employing clips to maintain the position of the structure. Preferably, the holder 54 is thermally conductive and provides structure temperature control, e.g., by a liquid heat exchange loop, employing a thermocouple positioned on the holder or on the structure itself. For many applications, it can be preferable that the holder also be electrically conductive to enable voltage charge control of the structure and to enable monitor of incident ion beam current.

The holder includes a central aperture 56 corresponding to the location at which an aperture is to be formed in the structure 10. With this configuration, a beam of ions 58 directed from the ion gun toward the structure 10 thins the structure to form therein an aperture, after which time the ion beam 58 traverses both the structure aperture and the holder aperture.

Referring to FIG. 3B, an electron flood gun 59 can be included in the arrangement to direct a beam of electrons at the structure being etched during the etch process. For structures such as a silicon nitride membrane that are electrically insulating, positive electrical surface charge can accumulate on the structure due to positively-charged ion beam irradiation. Electron beam irradiation of the structure can be carried out to neutralize this surface charge, if necessary for a given application.

If the thinning etch process is to be controlled by a feedback mechanism in accordance with the invention, then the stream of a species traversing the etched aperture is to be detected and quantified in the manner described below. If no such feedback control is desired for a given application, then no additional apparatus is necessary, and the sputtering can be carried out in a conventional sputtering chamber under conditions selected for a given etch.

In accordance with the invention, species detection and quantification systems can be included to provide a desired degree of feedback control. Given a scenario where the selected sputtering beam ions employed for the thinning etch are electrically charged, ion focusing optics 60 can be provided for focusing the ions once they traverse the aperture, to facilitate ion detection by a detector that is relatively distant from the structure aperture through which the ions traversed. X-Y deflection optics and Einzel lenses can be employed in conventional configurations to produce a desired focusing of the ions. In the conventional manner, optics design software can be employed to produce a customized focusing configuration for a given detection arrangement. It is to be recognized that such focusing configuration may not be required for configurations where the ion detection system is relatively near to the holder aperture.

If employed, the focusing configuration preferably directs the output ion beam to an ion energy analyzer 62 for filtering the beam for the selected species to be detected and quantified by, e.g., counting. In general, it can be expected that the ion beam sputtering process will include and produce a wide range of physical species and radiation, including, e.g., sputtered silicon nitride atoms, etch species scattering in the etch chamber, and X-rays emanating from the ion gun. To enable highly precise etch control, the species to be detected is preferably filtered out from the produced radiation, produced etch species, and background radiation. Such background can be minimized by, e.g., isolating the ion beam gun, the structure to be etched, and the downstream optics from further downstream components such as detectors, as described below, by an electrostatic energy filter or other suitable filter. In addition, it can be preferable to maintain the ion beam gun, structure, and optics at reduced temperature conditions in a suitable vessel, as shown in FIG. 3B, whereby thermal effects can be controlled. Such a cooling configuration is also useful to maximize cleanliness of the etch and beam detection environment and to control structure temperature. It can also be advantageous to maintain the structure at an elevated temperature to influence materials modification phenomena during ion irradiation.

The employment of an ion energy analyzer 62 or other species-specific filtering system is advantageous in that it enables redirection of a species to be detected out of the line of sight of the sputtering trajectory. The species detection location can then be distant and out of line from bombardment by background and produced radiation such as X-rays. For example, as shown in FIGS. 3A–3B, the electrostatic energy analyzer employed produces a 90° bend in the trajectory of the ion species to be detected, whereby that species is separated from the other species and radiation coming from the etched structure. If the detection resolution and speed desired for a given etch process do not require a low background noise environment, then the ion energy analyzer is not required for many applications.

The filtered species of interest output from the electrostatic energy analyzer is directed to a detector 64. For the detection of an electrically charged ion species, it can be preferable to employ a high-resolution, single ion detector, e.g., a Channeltron 4860 detector from Gallileo Electro-Optics of Sturbridge, Mass. Such a detector can be configured to produce one electrical output pulse per detected ion. Such single ion detection and associated counting can be preferred for many applications to enable nanometric-scale precision in production of a solid state feature such as an aperture. While a typical sputtering beam current density is about 10 ions/nm$^2$/sec, etching of a nanometer-range aperture requires counting of the passage of no more than about 10–20 ions through the aperture. Thus, a single ion detection and counting system, or another system of equivalent resolution, is preferred to reproducibly implement nano-regime control of feature production. If the features to be produced for a given application do not require nanometric dimensional control, then a more coarse detection mechanism can be employed.

Given a single ion detector configuration, a fast pulse amplifier 66 can be employed to modify the electrical output of the detector to facilitate an ion counting process. A suitable pulse preamplifier can be constructed in a conventional manner or a suitable commercial system, e.g., the VT120 Fast Preamp from EG&G Ortec of Oak Ridge, Tenn., can be employed. In one example scenario, given the production of a 10 mV ion detection pulse by the ion detector, the pulse amplifier 66 can be configured to amplify the pulse voltage to about 1 V. This amplified detection pulse is directed to a counting system, e.g., a universal counter such as the HF53131A by Hewlett Packard, for producing an electrical signal indicative of the number of detected ions. It is recognized that detection pulse amplification may not be required for a given pulse counter configuration, and that the pulse amplification, if implemented, is preferably controlled based on requirements of the counting system.

The electrical output of the pulse counter 68 is directed to a controller 70 that implements, e.g., monitor and control software for enabling an operator to monitor the thinning etch process in real time and for producing an ion gun control signal. In one example, the controller is implemented in software employing, e.g., Labview, from national Instruments of Austin Tex. Whatever controller implementation is selected, it preferably provides ion beam control signals based on the ion feedback. For example, the controller can be implemented to initiate ion beam sputtering of the structure for a specified time interval and to configure the counter to count the number of ions received at the detector during the specified time interval. At the end of the interval, the number of ions counted is determined by the controller and the extent of the aperture can at that point be calculated based on this ion count and the known ion flux. The number of ions counted during the interval is then employed by the controller to determine if a further interval of ion beam sputtering is to be initiated to continue etch of the structure.

In one advantageous configuration, a computer system including monitor, memory, and associated input/output and printing systems is provided for enabling visual monitoring and recording of the etch process progression. Display of the ion count rate and aperture extent over time, and storage of count rate and other system values can be preferable for many applications.

The output of the controller 70 is directed to an ion gun control system 72 for controlling the sputtering etch itself. In one example implementation, ion gun feedback control is effected by control of the ion gun's X-Y deflection plates to deflect the ion beam away from the structure 10 at the time when the desired aperture dimension is produced. This can be a preferable control technique because of the rapid speed at which the beam can be deflected, typically in much less than a millisecond. It is recognized, however, that alternative beam control mechanisms can be employed. For example, an electrostatic grid can be located between the gun and the structure holder. In this scenario, the grid is energized in response to an ion beam termination control signal to return the beam back toward the ion gun. In a further technique, the accelerating electron impact voltage of the ion gun can be controlled in response to an ion beam termination control signal to terminate production of the ion beam. These techniques are advantageous in that they suppress all sputtering after the desired aperture dimension is produced, whereby possible contamination of the sample is eliminated.

With a sputtering system and feedback/control hardware configuration in place, a feedback calibration curve can be produced for a given ion beam species, structure material, and aperture geometry to be produced. Such a calibration curve enables specification of the relationship between ion count number and/or rate and limiting aperture dimension, and can be established empirically, to specify for a particular structural material and thickness a relation between number of measured counts per time and actual limiting aperture dimension.

It is found that for many configurations, the relationship between limiting aperture dimension and ion count is generally linear. For this and other generally-predictable relationships, an extrapolated calibration curve can be produced based on a few measurements. To produce each such measurement, a thinning etch is carried out for a prescribed duration, during which an ion count is made and at the end of which an aperture dimension is physically measured by, e.g., transmission electron microscopy. Multiple etch durations and dimensional measurements can be carried out on a single aperture as that aperture is increased from etch to etch. A calibration curve can then be produced based on the ion count and aperture measurements and extrapolated to lower and higher ion counts. With such a calibration curve in hand, the controller system of the feedback configuration can be programmed to direct a controlling etch termination signal to the ion gun when the prescribed ion count corresponding to a desired aperture dimension is reached.

It is to be recognized that etch environment temperature and pressure, mechanical stress and temperature of the structure being etched, and feature dimensions and structural aspects can influence the relationship between detected ion count rate and physical feature dimensions. For example, the residual mechanical stress in a silicon nitride membrane can impact its etch characteristics. Similarly, the density of apertures in an array to be formed, the aperture proximity to each other, and other aspects can impact etch characteristics. It is therefore to be recognized that the calibration curve preferably is produced with consideration for various physical and etch environment parameters that can impact etch characteristics.

EXAMPLE 1

Figure 4A:
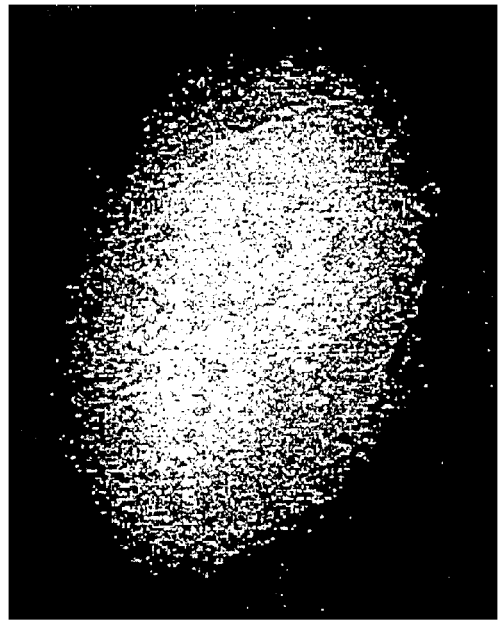
FIG. 4A is an electron micrograph of a cavity formed in a 500 nm-thick silicon nitride membrane in accordance with the invention.

A 50 nm-thick silicon nitride membrane having a cavity formed on one surface was produced by the process outlined in FIGS. 2A–G. The silicon nitride was deposited by low pressure chemical vapor deposition. The cavity bowl was etched in the membrane by a reactive ion etch process. FIG. 4A is an electron micrograph of the cavity formed in the membrane.

The membrane surface opposite that including the cavity was exposed to an argon ion beam etch at an energy of about 3 KeV, and a flux of about 3 $Ar^+sec/nm^2$. The ion beam diameter was about 200 μm and the membrane temperature during the etch was maintained at about −120° C. The ion beam was directed toward the membrane for 1 sec during each 5 sec interval. During the etch process, ion detection and counting was carried out.

Figure 4B:
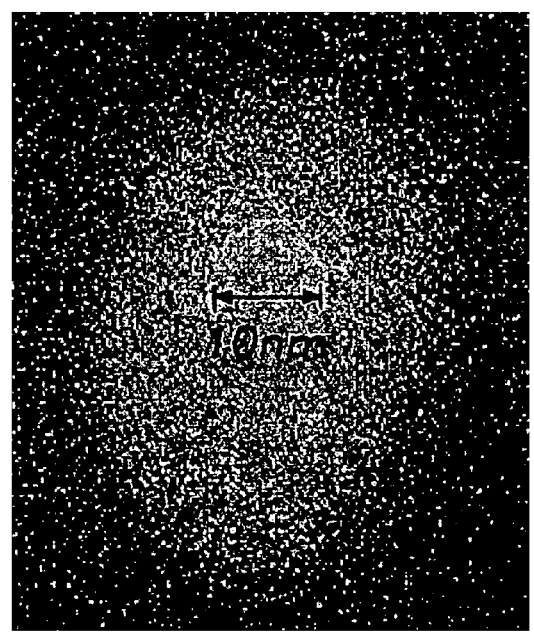
FIG. 4B is an electron micrograph of a 10 nm-wide aperture formed in a silicon nitride membrane by a process provided by the invention.
Figure 4C:
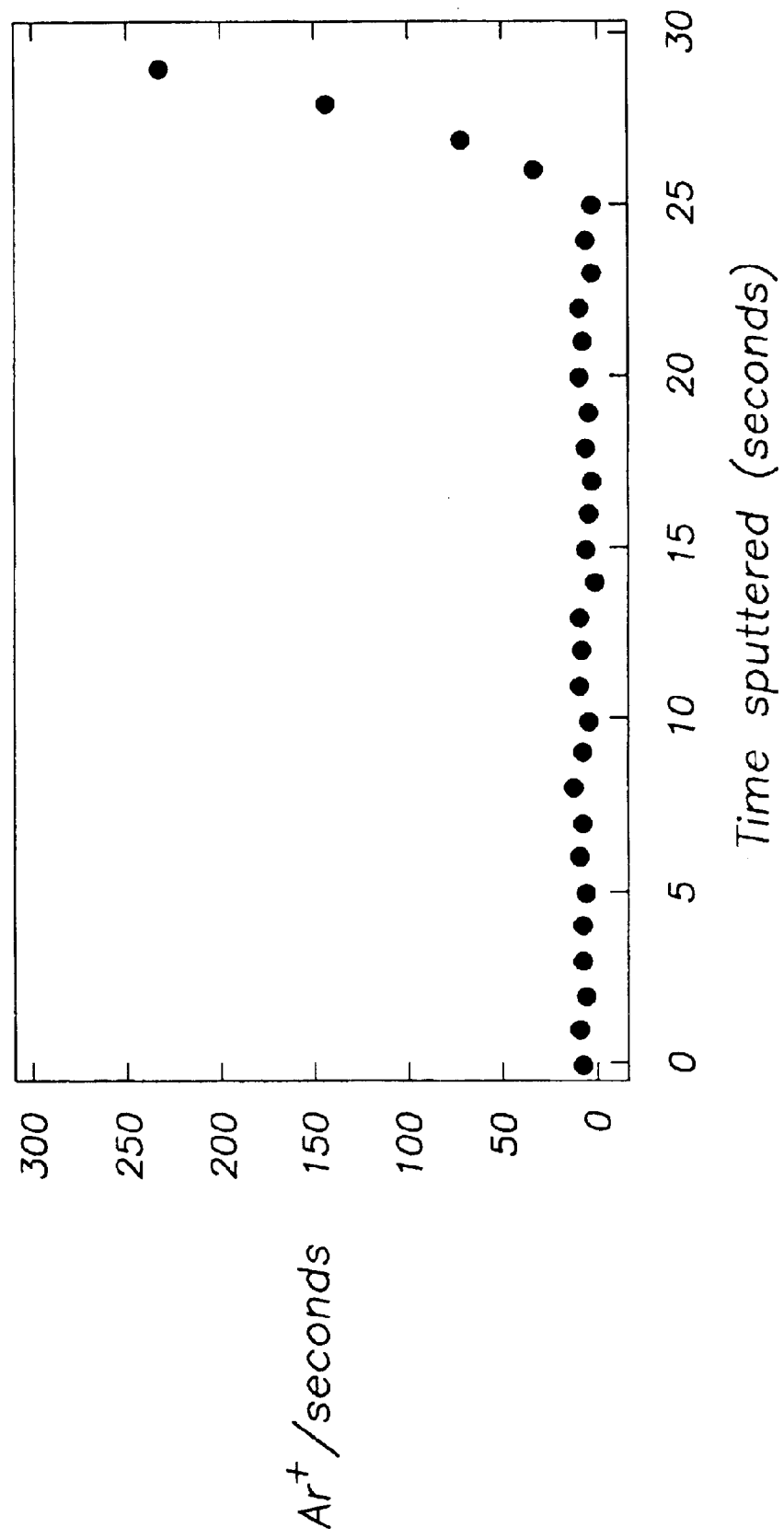
FIG. 4C is a plot of detected ion counts as a function of time for the aperture etch process that resulted in the aperture shown in FIG. 4B.

FIG. 4B is an electron micrograph of the membrane cavity including a 10 nm limiting aperture formed by thinning of the membrane. FIG. 4C is a plot of argon ion count/second as a function of sputtering time. This plot includes that time when the ion beam was directed to the membrane, not when the beam was deflected away from the membrane. As indicated by the plot, the number of counted ions/sec was substantially zero until at point in time, at 25 sec, when the limiting aperture was opened. Then as the limiting aperture diameter increased, the ion counts correspondingly increased. This enables control of the aperture formation process.

In this example, precise and controlled etch of the aperture was enabled by detection and counting of electrically charged ions that traversed the aperture once it was opened. Here the species operating as an etchant also operated as the species to be detected. In accordance with the invention, this dual role of the ion beam is not in general required. In an alternative scenario provided by the invention, the etchant species is selected and operates distinctly from the detection species. For many applications, such a decoupling of the etchant and detection species can be advantageous in enabling a broader range of candidate species for both etchant and detection species.

Considering an atom beam etch species, if the beam is electrically neutral rather than electrically charged, detection of the atoms can be difficult. A distinct non-etching detection species such as an electron beam can in this case advantageously be employed for controlling formation of a pre-specified aperture diameter. Such a scenario can be preferable where the structure being etched may become electrically charged by the impinging sputter beam, thereby warranting the use of an electrically neutral beam. For many applications, it can be preferable to employ an electrically charged detection species, for facilitating beam bending, filtering, and detection and counting with conventional techniques. Electrically neutral detection species can be employed, however, when such is optimal for a given application. For example, laser fluorescence of electrically neutral transmitted atoms can be employed for detecting and counting control functions.

When employed, a separate detection species is preferably one that can be directed in some manner toward a feature being produced and whose movement in the vicinity of the feature is indicative of changing dimensions of the feature. This enables detection of the species in a manner that is indicative of changes in the feature's dimensions. For example, in the case of formation of a membrane aperture, direction of an electron beam toward the membrane, such that electrons traverse the membrane aperture once it is formed, enables counting of electrons in the manner of ion counting described above. The invention does not require the use of a single detection species; more than one detection species can be employed. For example, X-rays produced by the ion gun can be monitored as the structure thins to predict and indicate a the time of a further aperture formation event. Thereafter ions, electrons, or other species can be employed to monitor changes in aperture diameter. Neutral species and other species suited to a given application can similarly be employed together to provide precise detection and feedback mechanisms.

In addition, the invention does not require that the detection species be directed orthogonally to the plane of a feature being produced. For example, electron beam diffraction detection and the diffraction patterns produced by a material can be employed as a feedback mechanism. In such a case, e.g., where a feature in an upper layer is formed by removal of the upper layer to expose a lower layer or substrate, detection of the electron beam diffraction pattern characteristic of the lower layer can be employed as the feedback mechanism. Here the electron beam makes a glancing angle with the material. Similarly, in the case of formation of, e.g., an aperture, diffraction can be detected as a function of the aperture diameter by diffraction rings indicative of changes in aperture periphery. The diffraction feedback mechanism here occurs at the aperture periphery rather than as a trajectory through the aperture.

In a further example, an electron beam can be directed parallel to the upper structure surface being thinned in formation of an aperture, whereby the withdrawal of surface material is indicated by an increase in electron count in a direction parallel to that surface.

The invention contemplates alternative detection species. For example, atoms in a meta-stable state, e.g., an electronic meta-stable state, can be directed toward a feature being formed and detected once past the feature. Such meta-stable atoms, e.g., excited states of helium or argon, are electrically neutral and do not decay until hitting a solid surface, at which time an electron is liberated and can be detected and counted. Whatever detection species is selected, it preferably is one that can be detected and counted on a time scale that is commensurate with the desired dimensional scale of control in the feature being produced. For example, where nanometric feature dimensions are of importance, microsecond detection and counting processes are preferable to enable high sensitivity and resolution in the feedback mechanism. Less strict sensitivity and resolution requirements need be placed on detection species for micro- and macro-scale feature control.

The invention contemplates application of physical species detection and counting for feedback control in a wide range of fabrication processes. Many fabrication processes that are conventionally carried out in open loop fashion, i.e., without feedback control, can be adapted to enable nanoscale dimensional feature control with the incorporation of the highly sensitive and precise feedback mechanisms provided by the invention. For example, in the aperture formation process described above, reactive ion etching in a plasma, rather than sputter etching, can be employed to thin a structure surface in formation of a limiting aperture. In such a plasma etch process, the structure surface including a cavity is isolated from the plasma environment by a suitable fixture. The opposing structure surface is fully exposed to the plasma environment. As the plasma etch progresses to thin the structure and eventually produce a limiting aperture and growing aperture, ions traversing the aperture are detected by, e.g., a channeltron positioned on the isolated side of the structure. Accordingly, in the manner of the ion sputtering etch described above, feedback control can be imposed on the plasma etch process based on the detection and counting of plasma ions traversing the aperture.

In a further example process contemplated by the invention, physical detection and feedback control can be imposed on a wet etch process employed to produce a feature. For example, in formation of an aperture in a structure, electrodes can be provided near to the cavity formed in the structure. Here the structure surface opposite the cavity is exposed to a wet etch environment, e.g., an electrochemical environment, and the structural surface which includes the cavity is isolated from the etch environment. As the wet etch progresses to thin the structure and open an aperture, ions in the liquid that traverses the aperture can be detected and counted at the cavity-side electrodes. This enables feedback control for terminating the electrical stimulus of the etch at a time when the desired aperture dimension is attained.

The invention contemplates implementation of physical species detection and feedback process control for enabling fabrication of a wide range of structural, solid state features. The feedback mechanism is not limited to the aperture formation process described above. As explained above, an aperture, slit, trench, hole, or gap between two feature edges can be precisely formed, by any of a wide range of processes, in a precise and controllable manner with the feedback mechanisms of the invention.

For example, in a membrane aperture formation process employing, e.g., focused ion beam or plasma etching techniques where a hole is formed directly through the thickness of the membrane from one surface to the other of the membrane, feedback can be employed to control and monitor the formation. Similarly, the invention contemplates a membrane aperture formation process where a cavity is formed in one surface of the membrane and then that membrane surface, including the cavity, is exposed to, e.g., an ion sputtering etch. Because the thickness of the membrane between the cavity bottom and the opposing surface is much less than at other membrane regions, such etching opens a limiting aperture at the base of the cavity before completely etching away other regions of the membrane. The feedback mechanisms of the invention enable precise control and monitoring of this process.

EXAMPLE 2

Figure 5A:
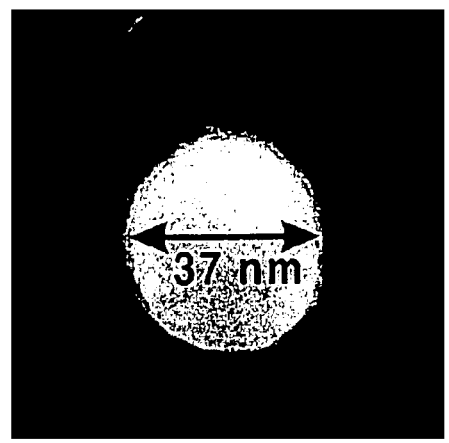
FIG. 5A is an electron micrograph of a 37 nm-wide aperture formed in a 500 nm-thick silicon nitride membrane in accordance with the invention.

A silicon nitride membrane of about 50 nm in thickness was produced in the manner of FIGS. 2A–2E. An aperture was formed through the entire thickness of the membrane by reactive ion etch. This resulted in a 37 nm-wide aperture, an electron micrograph of which is shown in FIG. 5A. The membrane and aperture were then exposed to an argon ion beam at a flux of about 1.7 $Ar^+/nm^2/sec$ and an energy of about 3 KeV. The ion beam was directed toward and away from the membrane to sputter for 1 second during each 5 second interval. The membrane was maintained at a temperature of about −102° C. during the ion beam exposure.

Figure 5B:
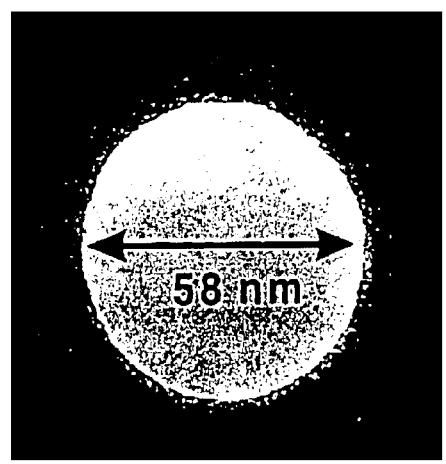
FIG. 5B is an electron micrograph of the aperture of FIG. 5A enlarged to 58 nm in width by a process provided by the invention.
Figure 5C:
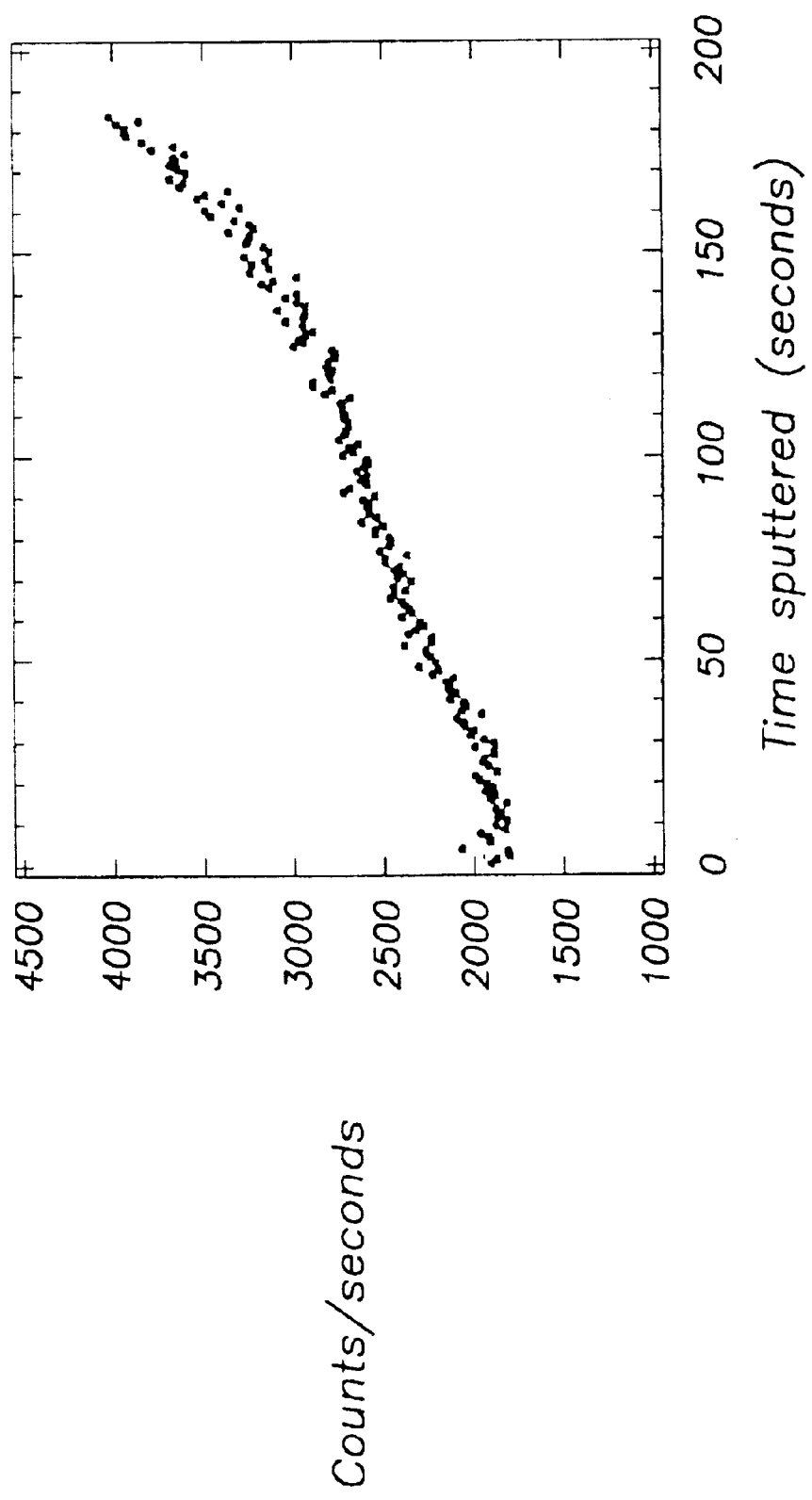
FIG. 5C is a plot of detected ion counts as a function of time for the aperture etch process that resulted in the aperture increase from that shown in FIG. 5A to that shown in FIG. 5B.

FIG. 5B is an electron micrograph of the 58 nm-wide aperture that resulted from 180 seconds of sputtering. FIG. 5C is a plot of counted ions/sec as a function of time. A generally linear relationship between ion counts as a function of time is demonstrated.

The invention does not require that the process being controlled by feedback be a subtractive process as in Example 2; additive processes can also be controlled by the feedback techniques of the invention. For example, an aperture, trench, or hole of a given dimension can be diminished or narrowed, by a suitable process, during which the physical species detection and feedback process control of the invention is imposed to control the diminishing process.

Sintering, heating, material deposition, material growth, and other suitable processes are contemplated as being controllable by the feedback mechanism of the invention. Similarly, oxidation, swelling, material flow and transport as described in detail below, condensation, evaporation, electroplating, ion- or electron-assisted deposition or growth, and other such additive processes can be controlled in accordance with the invention. The only requirement of the process to be controlled, whether additive or subtractive, is that the process accommodate the introduction of some detection species near to the structural feature being processed in a manner that enables detection of that species as an indicator of changing feature dimensions. As explained above, the features can be produced in a membrane, in a layer or layers provided on a support structure, or in a structure itself, e.g., a silicon wafer. Whether the process being controlled is additive or subtractive in nature, the advantages of the control processes of the invention can be most fully exploited and realized in the formation of nanometric scale feature dimensions and dimensional tolerances.

This capability can be particularly advantageous for producing a field of nanometric features, e.g., in formation of a lithographic mask plate. Here, e.g., a starting membrane can be processed with selected geometries to ultimately form wires, pads, and other mask plate geometries by additive or subtractive processes. This enables precise formation of the mask plate features in an efficient and effective process.

In another aspect of the invention, the inventors herein have discovered that the conditions of interaction between an ion beam and a solid can be controlled for manipulating nanoscale feature dimensions in solid state materials. These controlled ion beam interaction techniques enable solid state material topology to be adjusted, rather than necessarily removed. Specifically, under selected process conditions provided by the invention, solid state material can be caused to transform such that feature edge locations are precisely and controllably produced and/or modified by atomic transport mechanisms that are locally additive or subtractive.

Figure 6A:
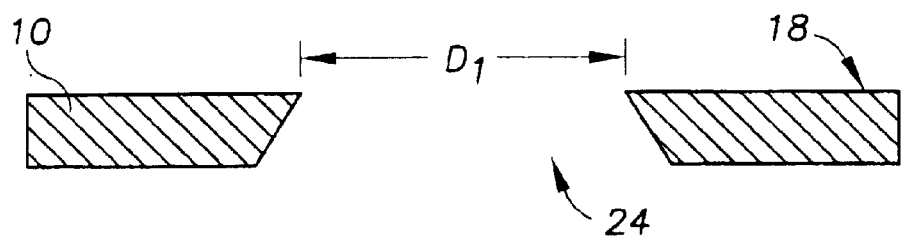
FIGS. 6A–6C are schematic cross-sectional views of stages in the reduction of a limiting aperture diameter by a process provided by the invention.
Figure 6B:
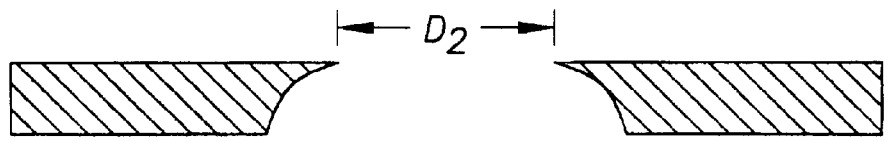
Figure 6C:
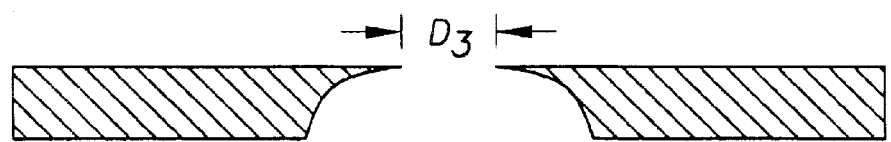

Referring to FIGS. 6A–6C, in a first example of this ion beam feature control, a limiting aperture 24 in a structure 10 is caused to be adjusted from a first diameter, $D_1$, to a smaller diameter, $D_2$ or $D_3$. The starting aperture is formed in a selected structure in any suitable fashion, e.g., by the methods described above and shown in FIGS. 1A–1D and FIGS. 2A–2G, in, e.g., a membrane, layer, substrate, or other structure. The structure surface 18 in which the limiting aperture was formed is then exposed to ion beam irradiation, employing, e.g., the system described above and illustrated in FIGS. 3A–3B.

As shown most dramatically in FIG. 6C, for selected ion beam irradiation conditions, the inventors have discovered the unexpected result that the material is added to the periphery, or boundary, of the limiting aperture 24 exposed to the irradiation, causing the diameter of the limiting aperture to decrease. This condition can be predictably and precisely imposed by enforcing structure temperature, ion flux rate, and ion energy conditions conducive to material addition at the aperture rim. Given that the ion beam irradiation is generally considered to be a sputtering/material removal process, it is particularly unexpected that this material movement and addition condition can effectively progress, even in the presence of the atomic sputtering erosion, to result in a change in the physical dimensions of a feature.

EXAMPLE 3

Figure 7A:
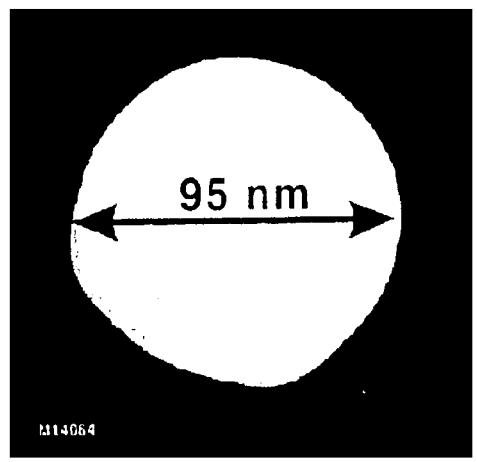
FIG. 7A is an electron micrograph of a 95 nm-wide aperture formed in a 500 nm-thick silicon nitride membrane in accordance with the invention.

A silicon nitride membrane of about 500 nm in thickness was produced in the manner of the process outlined in FIGS. 2A–E. An aperture was formed through the entire thickness of the membrane by reactive ion etching. FIG. 7A is an electron micrograph of the 95 nm-wide aperture that resulted from the etch.

The membrane and its aperture were then exposed to an argon ion beam flux at an energy of about 3 KeV, and a flux of about 47 Ar$^+$/sec/nm$^2$. The membrane was maintained at a temperature of about 20° C. during ion flux exposure. The ion beam was directed to the membrane for 250 ms for each 1 sec time interval.

Figure 7B:
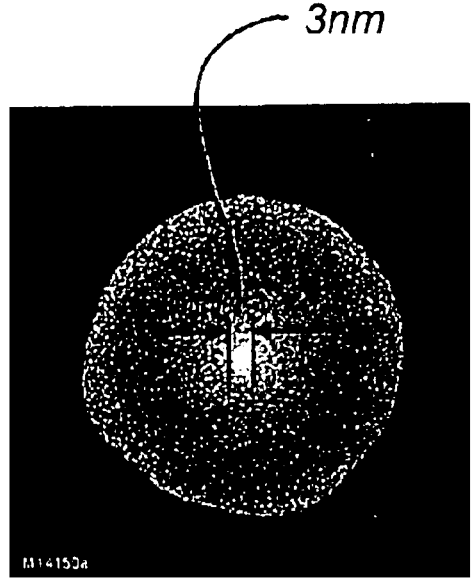
FIG. 7B is an electron micrograph of the aperture of FIG. 5A reduced to 3 nm in width by a process provided by the invention.
Figure 7C:
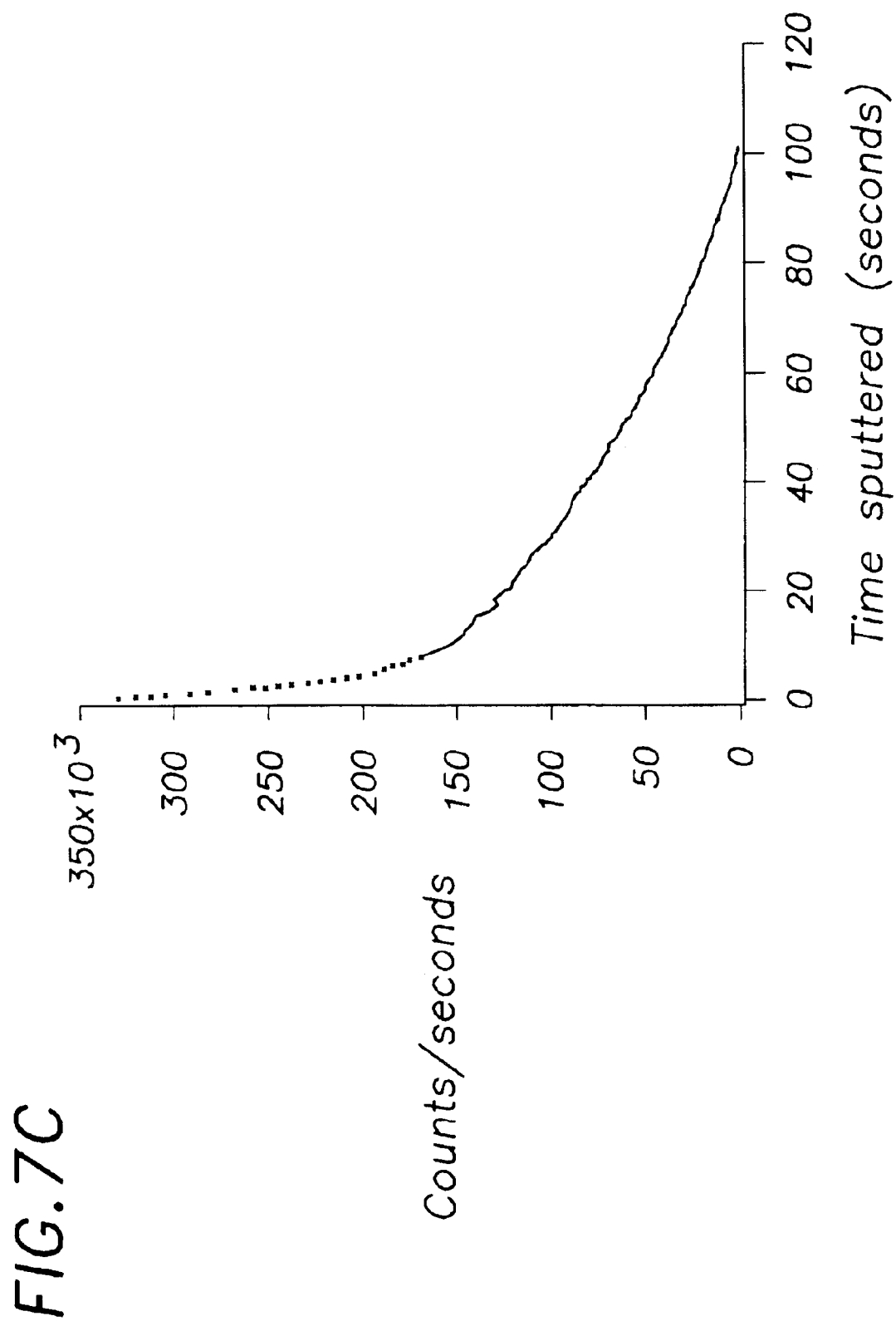
FIG. 7C is a plot of detected ion counts as a function of time for the aperture etch process that resulted in the aperture decrease from that shown in FIG. 7A to that shown in FIG. 7B.

FIG. 7B is an electron micrograph of the membrane after exposure to the argon ion beam reduced the aperture diameter to about 3 nm. FIG. 7C is a plot of counted argon ions/sec as a function of time. A generally linear count rate is indicated for midpoints in the process.

Without being bound by theory, the inventors herein understand that the mechanisms underlying the ability of an ion beam to cause material build up at an ion-irradiated aperture rim may be related to atomic transport through the bulk of the structure; ion-induced changes in viscosity, electronic surface charge, mechanical stress generation, and lateral swelling of the structure; and/or atomic surface transport caused by ion-induced surface atom excitation or supersaturation of mobile adsorbed ionic species on the structure surface. At sufficiently low ion energies the ion penetration depth is much less than the structure thickness, resulting in a domination of surface transport processes. The invention does not require a specific material transformation mechanism, but rather, provides distinguishing process control parameters that impose predictable material transformation results.

Considering the process parameters to be controlled, it is found that the temperature of the structure being exposed to the ion beam irradiation directly impacts the ability to impose material movement and the rate at which material moves. It is found that for a specific structural material, there is a characteristic temperature above which material of the structure is found to move, resulting in an adjustment, or change, in feature dimensions and below which material is instead removed by sputtering from the structure. For given ion beam energy and flux conditions, control between material removal and dimensional feature adjustment can therefore be imposed by structural temperature control.

EXAMPLE 4

Figure 8:
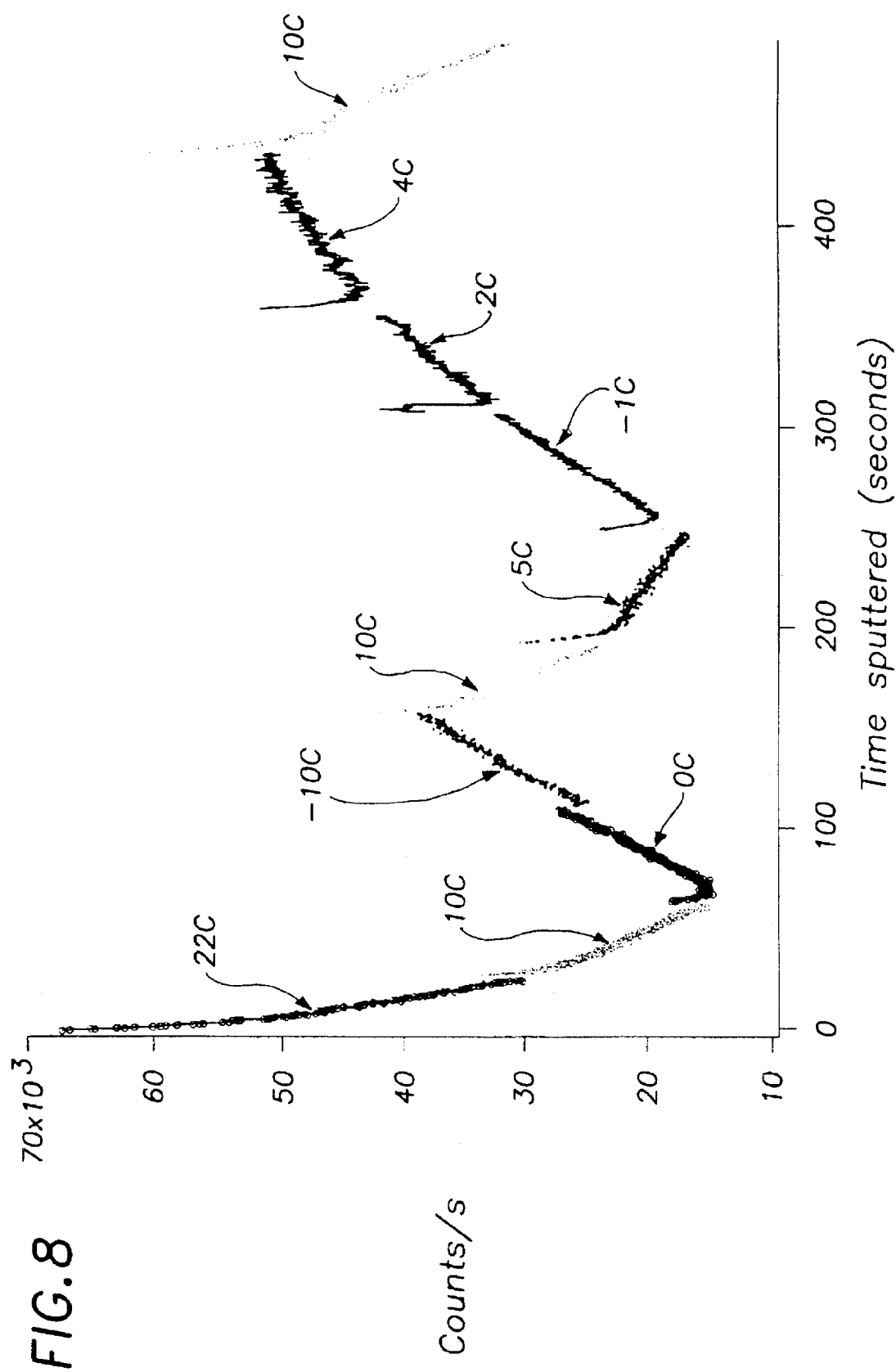
FIG. 8 is a plot of detected ion counts per second as a function of ion sputtering time of a square aperture, initially of about 72 nm×72 nm in area, in a silicon nitride membrane of 500 nm in thickness, subjected to the mass transport processes of the invention under various temperatures.

Referring to the graph of FIG. 8, there is plotted the ion counts/second detected by an ion sputtering system like that of FIG. 3A as a function of time for a 500 nm-thick silicon nitride membrane in which was initially fabricated a square aperture of about 72 nm in length. The membrane was fabricated based on the process shown in FIGS. 2A–2F and the aperture was fabricated by a focussed ion beam directed at the membrane to form an aperture that extended completely through the membrane. Each region of the graph indicates the temperature at which the membrane was maintained during bombardment by an argon ion beam. The beam flux was 14 Ar$^+$/sec/nm$^2$ and the beam energy was 3 KeV. The on/off duty cycle of the ion beam being directed toward the membrane was such that the beam was directed to the membrane for 200 msec during each 1 sec interval.

As a function of time, an increase in ion count/second indicates an increase in the aperture dimension, while a decrease in ion count/second indicates a decrease in the aperture dimension. The plotted data clearly indicate an increasing rate of aperture shrinkage under the ion beam irradiation as the membrane temperature is increased above about 5° C. In contrast, at membrane temperatures below about 4° C. the aperture dimension increases rather than decreases. At membrane temperatures between about 0° C. and about −10° C. no appreciable temperature dependence in the rate at which the aperture dimension decreases is indicated.

With this experimental data, it is indicated that for a silicon nitride membrane, two distinct temperature regimes exist; the first temperature regime, at or above about 5° C., imposes material movement and feature addition by ion beam irradiation, the second temperature regime, at or below about 4° C., imposes material sputtering and removal by ion beam irradiation, both regimes for given ion beam species, flux, and energy conditions. This analysis for a silicon nitride membrane is an example of the empirical analysis contemplated by the invention to determine that temperature above which a material of interest can be made to move and augment features. It is recognized that this transition temperature can vary widely from material to material.

The plotted data also indicate that within the regime for imposing material movement and addition, the rate of material transport in altering feature topology is temperature dependent. At relatively higher temperatures, the transport process proceeds more rapidly than at relatively lower temperatures. Knowledge of this temperature-dependent transport rate enables precise process control and characterization.

EXAMPLE 5

Five silicon nitride membranes of about 500 nm were fabricated in the manner of the process outlined in FIGS. 2A–E. Apertures each of about 1400 nm$^2$ in area were produced in the membranes by focused ion beam etching. The membranes were then exposed to an argon ion beam at an energy of about 3 KeV for various total doses at five ion beam fluxes. Each membrane was maintained at a temperature of about 22° C. during the ion beam exposure. Each ion beam exposure was controlled to sputter for 200 msec during each 1 second interval.

Figure 9A:
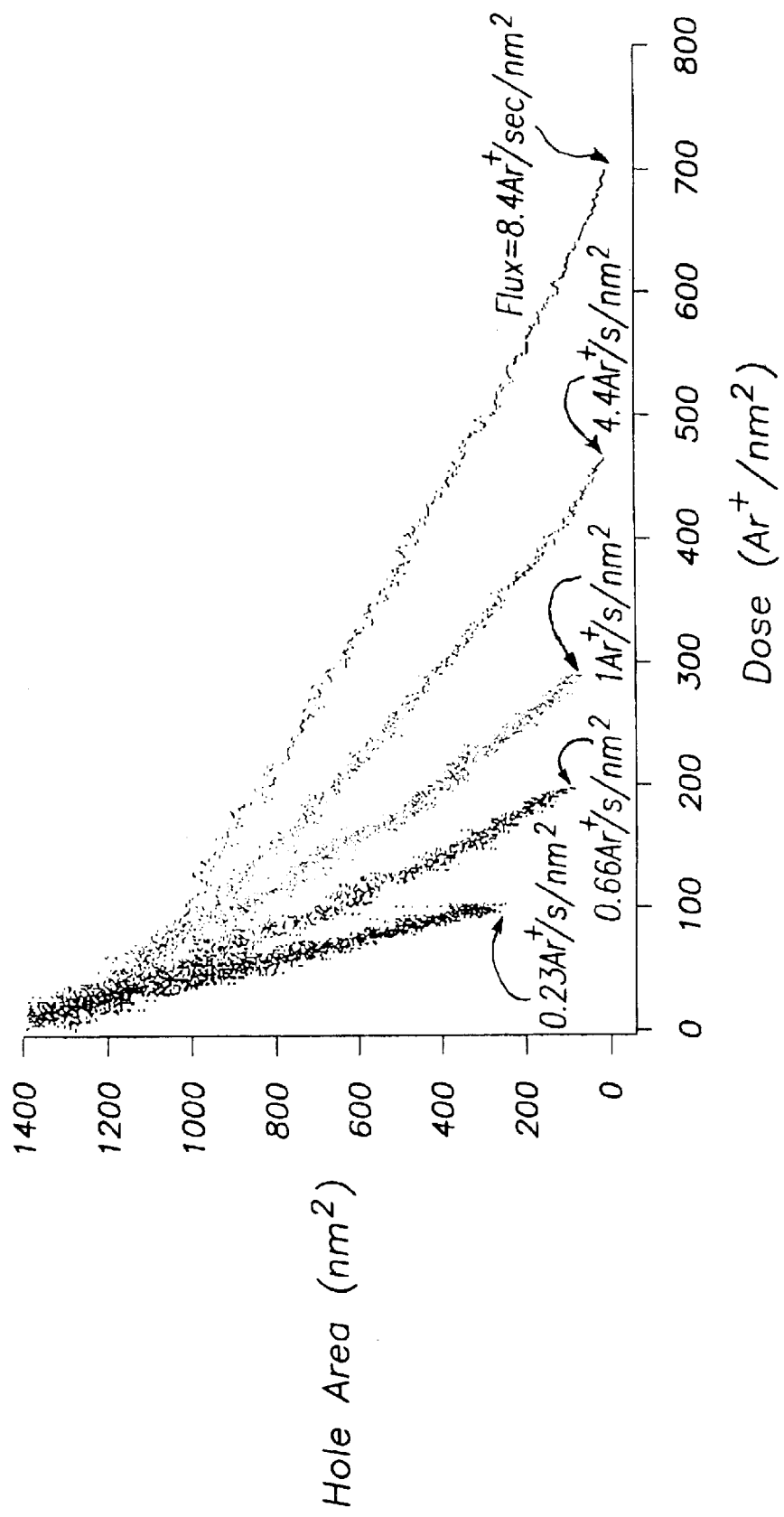
FIGS. 9A–9B are plots of aperture area as a function of total ion dose for five different ion fluxes and aperture area decrease per dose as a function of ion flux, respectively, for an aperture having an initial area of about 1400 $nm^2$, for the material transport processes provided by the invention.
Figure 9B:
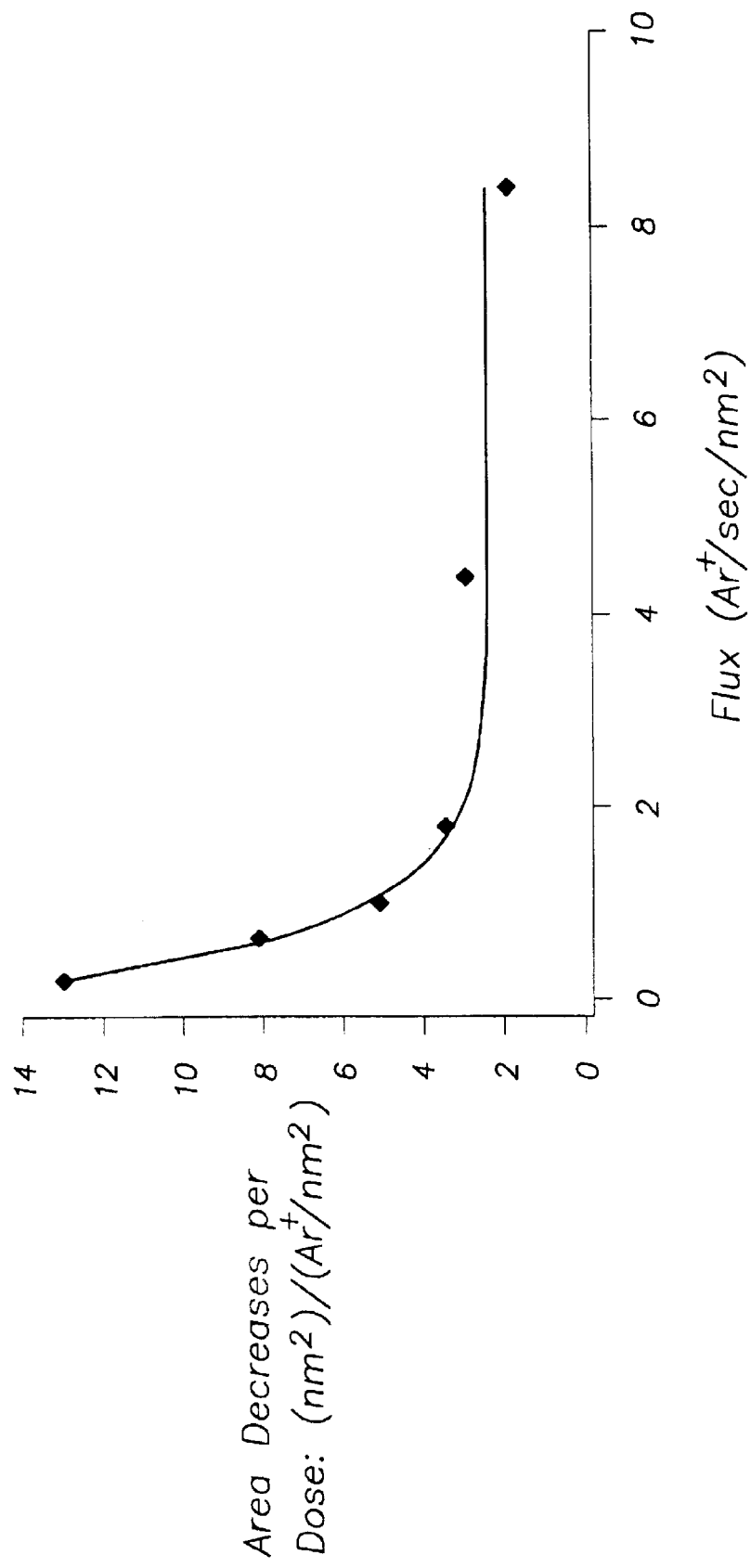

Referring to the graphs of FIGS. 9A–9B, there is plotted the area of the apertures in nm$^2$ as a function of total argon ion beam dose, in ions/nm$^2$, for five different argon ion beam fluxes, and the aperture area decrease per dose, as a function of argon ion beam flux, respectively. From the plotted data, it is indicated that as a function of total argon ion beam dose, the aperture shrinks more rapidly at low incident fluxes relative to higher incident fluxes. In other words, the lower the flux, the less dose is required to shrink an aperture. The strong nonlinearity indicates that the amount of material mass transport produced by the ion beam irradiation per incident ion may be suppressed at high incident fluxes. This characterization enables operation at a selected mass transport rate. In a manner analogous to the temperature dependence analysis provided above, the invention contemplates empirical analysis of flux dependence for a selected material, to enable precise control of the material movement.

EXAMPLE 6

Figure 10A:
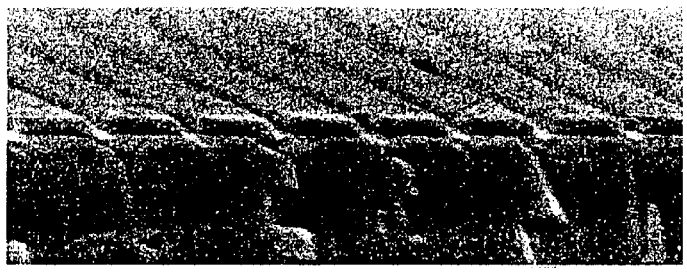
FIGS. 10A–10C are scanning electron micrographs of a trenched silicon nitride layer exposing the underlying silicon wafer on which the layer was deposited, partial fill-in of the silicon nitride trenches as a result of the material transport process conditions provided by the invention, and partial sputter etch removal of the upper trench layer as a result of the sputtering conditions provided by the invention.

A 50 nm-thick layer of silicon nitride was deposited by low pressure chemical vapor deposition on a silicon wafers. The silicon nitride layer was patterned by electron beam lithography to produce trenches of about 50 nm in width through the entire thickness of the silicon nitride layer. The bottom of each trench thereby exposed the underlying silicon surface. FIG. 10A is a scanning electron micrograph of the trenched silicon nitride layer on the silicon wafer.

Figure 10B:
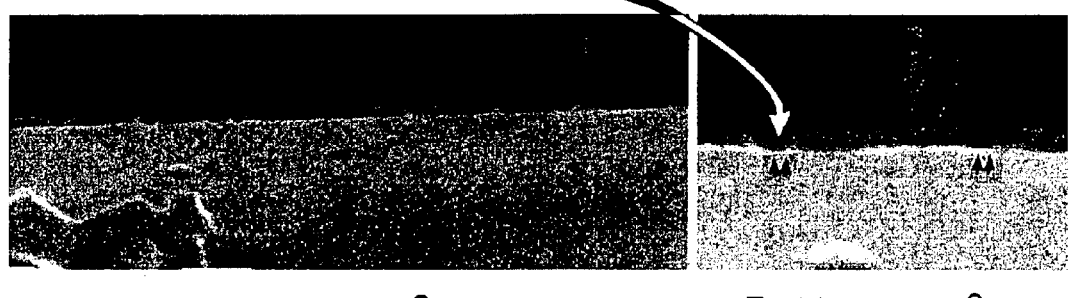

The trenched silicon nitride layer was exposed to an argon ion beam at an energy of about 3 KeV and a flux of about 20 Ar$^+$/nm$^2$/sec, where the ion beam was sputtering for 0.5 seconds for each 2 second interval. The silicon wafer was maintained at a temperature of about 20° C. during the ion beam exposure. FIG. 10B is a scanning electron micrograph of the trenched silicon nitride layer after about 200 seconds of sputtering. Note that silicon nitride material has been moved to the trenches, whereby the trenches have been partially filled in. This indicates that for the process conditions here employed, material is transported from the silicon nitride layer to the trenches.

Figure 10C:
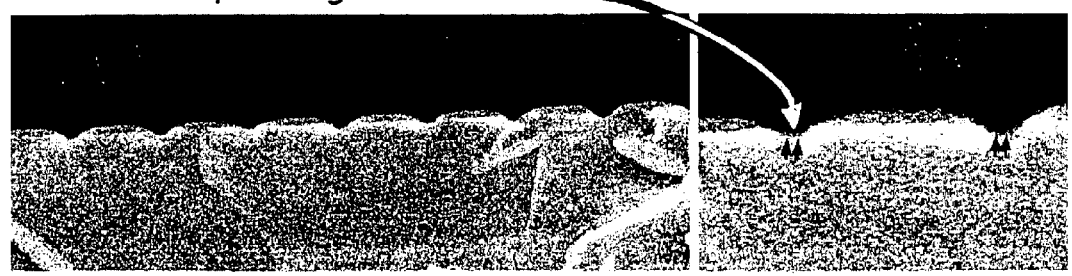

A second 50 nm-thick trenched silicon nitride layer like the one just described was exposed to an argon ion beam at an energy of about 3 KeV and an ion flux of about 30 $Ar^+/nm^2$/sec, with the ion beam sputtering for one second during each two second interval, for a total sputtering time of about 300 seconds. The silicon wafer was maintained at a temperature of about $-100°$ C. during the ion beam exposure. FIG. 10C is a scanning electron micrograph of the trenched silicon nitride layer. Here, the silicon nitride material at the top of the trenches has been etched away, as indicated by the rounding of the trench edges, but the bottom of the trenches are not at all filled in.

This example demonstrates the temperature control that can be imposed to predictably produce material transport and feature adjustment or material removal by sputtering as desired for a given application.

Turning to additional material transport control mechanisms provided by the invention, it is understood that the energy of the ion beam can impact the nature of material transport. Specifically, for a given structural material and temperature, a given ion beam current density, and a given time structure of the ion beam exposure, as discussed below, there exists an ion beam energy above which material transport is effectively induced in the manner described above and below which sputtering in the conventional manner occurs. This juncture between the two distinct operational regimes can be empirically determined for a given material and ion beam exposure system, and can be employed as an important control technique for precisely enabling and disabling the material transport processes.

Further in accordance with the invention, it is found that the time structure of the ion flux exposure, i.e., the sequence of intervals in which the ion beam is controlled to enable interaction with a material and then controlled to not interact with the material, impacts the nature of material transport and dimensional feature change. Specifically, the imposition of an on/off duty cycle on the ion flux is found to impact the ability to cause material movement and corresponding dimensional feature change.

EXAMPLE 7

A 500 nm-thick silicon nitride membrane was produced in the manner of the process outlined in FIGS. 2A–E. A 95 nm-wide aperture was formed through the entire thickness of the membrane by focused ion beam etch. The membrane and aperture were then exposed to an argon ion beam at an energy of about 3 KeV and a flux of about 14 $Ar^+$/sec/$nm^2$. The membrane was maintained at a temperature of about 16° C. during the ion beam exposure. During the exposure, the amount of time that the ion beam was directed to the membrane was varied. Six different time structures were employed: 100 msec on for each 1 second interval; 200 msec on for each 1 second interval; 400 msec on for each 1 second interval; 600 msec on for each 1 second interval; 600 msec on for each 2 second interval; and 600 msec on for each 4 second interval. During the ion beam exposure, ion detection and counting was carried out as an indication of the reduction or enlargement of the aperture in response to the various ion beam exposure cycles.

Figure 11:
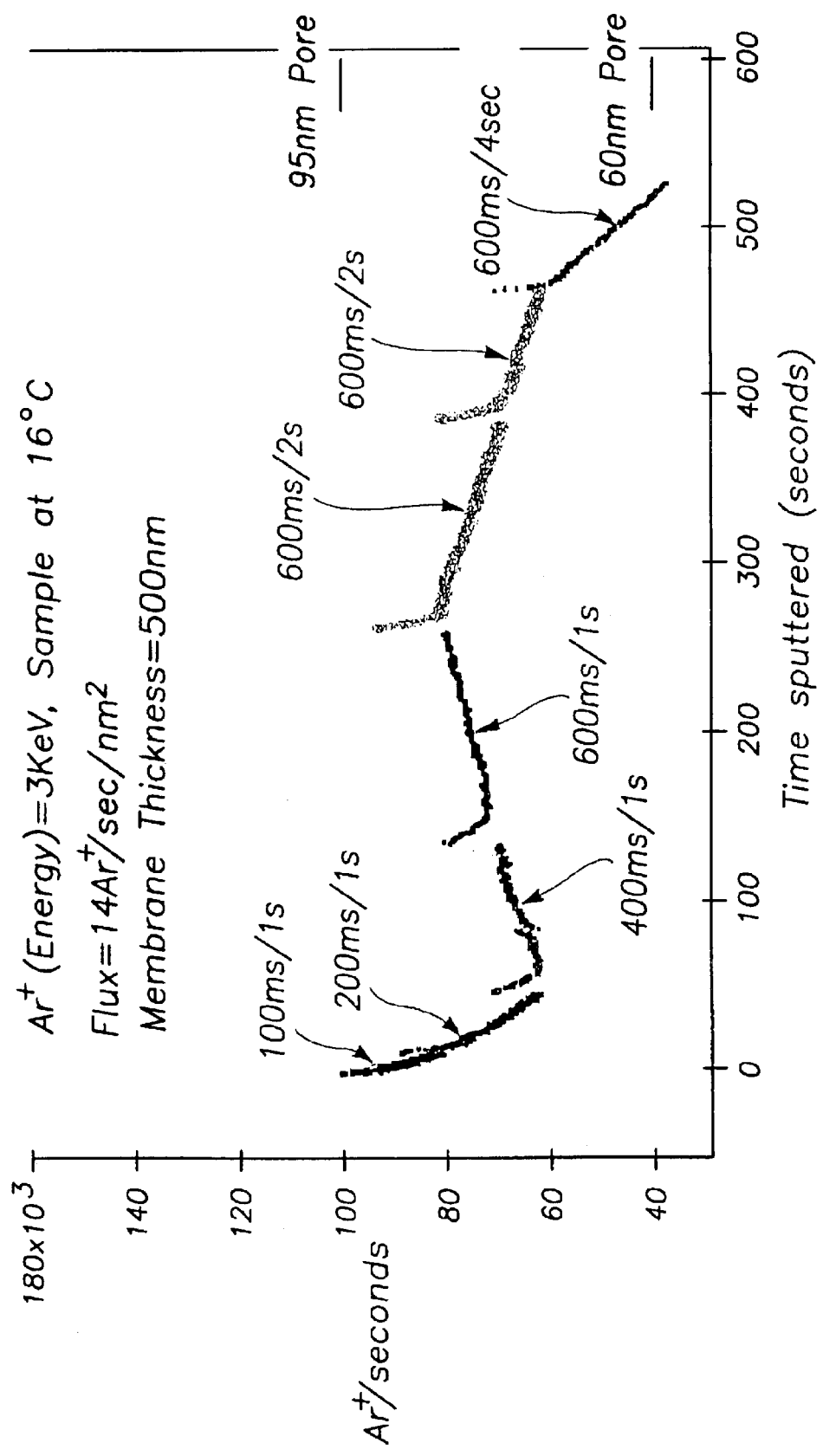
FIG. 11 is a plot of counted ions/second traversing an aperture as a function of time for various ion beam exposure cycles.

FIG. 11 is a plot of argon ions counted/second as a function of sputtered time. The plot indicates that the 400 msec/1 second interval and the 600 msec/1 second interval time structures increased the aperture diameter, while all other time structures decreased the aperture diameter. This demonstrates that at about room temperature, control between material transport processes and sputtering processes can be achieved by control of the ion beam exposure time structure.

The ion detection and counting mechanism of the invention for imposing feedback control on ion irradiation mass transport is advantageous for many applications for enabling precise feature formation, but is not required by the invention. Once a mass transport process is characterized, and for processes that do not require very fine feature control, feedback control of the system may not be required. All that is required is the exposure of the material to an ion beam under conditions that impose processes such as mass transport for adjusting dimensions of structural features of the material by local material addition or subtraction.

This structural material adjustment process provided by the invention can be applied to a wide range of structural features, including holes, slits, apertures, and gaps in general, and in trenches and other such features where a distinct feature rim or wall is present and can be adjusted. It further can be applied to fabrication of protruding features such as hillocks and asperities.

In one example of such a fabrication technique, the ion flux and dose and the temperature of a membrane are selected to produce a protrusion on the membrane by exposure to ion beam flux. One membrane surface is exposed to the ion beam flux under the selected conditions. This results in formation of a protrusion on the membrane surface opposite that exposed to the ion flux.

EXAMPLE 8

A silicon nitride membrane of about 500 nm in thickness was produced by a LPCVD process following the fabrication sequence outlined in FIG. 2. The membrane was exposed to a gallium ion beam at an energy of about 50 KeV and a dose of about 4 nanocoulombs/$\mu m^2$. Five different isolated exposure areas on the membrane were defined, namely, 0.12 $\mu m^2$, 0.14 $\mu m^2$, 0.16 $\mu m^2$, 0.18 $\mu m^2$, and 0.20 $\mu m^2$.

Figure 12:
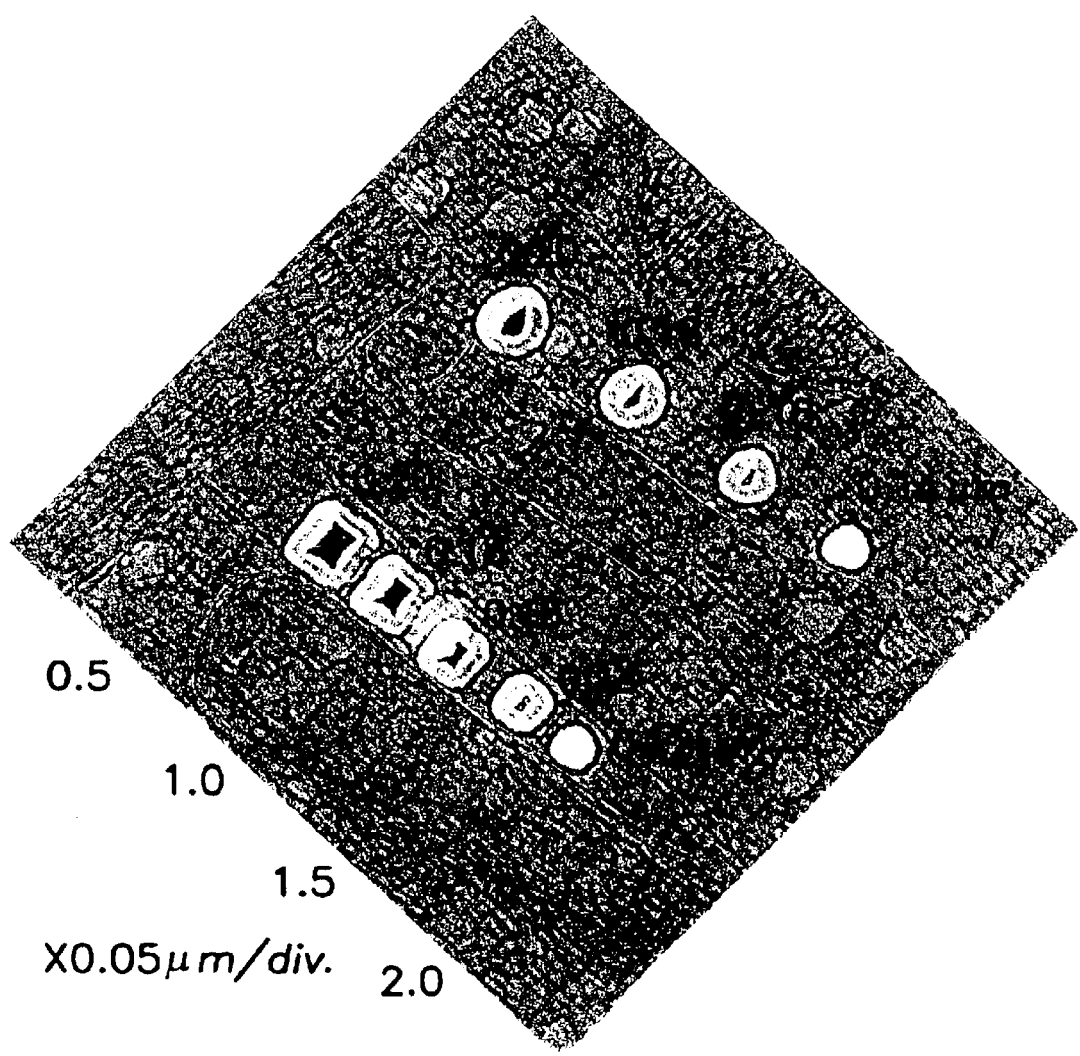
FIG. 12 is an atomic force micrograph of a silicon nitride membrane one surface of which was exposed to a focused ion beam to produce apertures and protrusions on the membrane surface opposite that exposed to the ion beam.

FIG. 12 is an atomic force micrograph of the nitride membrane surface opposite that which was exposed to the gallium ion beam. In this image, brightness level corresponds to topology; the brighter a region in the image, the "taller," or higher, is the topology of that region. As noted in the image, both of the 0.16 $\mu m^2$, 0.18 $\mu m^2$, and 0.20 $\mu m^2$ membrane areas, and one of the 0.14 $\mu m^2$ membrane areas were opened by the ion beam exposure, i.e., an aperture through the thickness of the membrane resulted from the ion beam exposure in that area. The other 0.14 $\mu m^2$ membrane area and the 0.12 $\mu m^2$ membrane area were not opened by the ion beam exposure and instead exhibit hill-like protrusions formed on the membrane surface opposite that exposed to the ion beam. This example demonstrates that dose can be controlled to cause mass transport in a manner that produces a protrusion on the surface of a structure. This example further demonstrates that the ion beam species can impact the nature of feature formation and adjustment; in this example gallium ions were employed as opposed to the argon ions employed in earlier examples. It is understood in accordance with the invention that ion species can be selected to control aspects of feature formation processing. Similarly, it is understood in accordance with the invention that the ambient gas species present during the ion interaction with a material can be selected to control the nature of the interaction.

The features formed by and/or having dimensions adjusted or changed by the processes of the invention can be provided on the surface of a structure, in a layer provided on a support structure or a free-standing membrane, or other surface which can be irradiated by an ion beam. Composite material structures can be processed. There is no restriction on the fabrication sequence employed to produce the starting structures for which dimensional adjustment is to be carried out.

The invention provides a model of the various ion beam processes described above for enabling control of the process parameters. Such process control provides an ability to, in effect, ion beam sculpt nanoscale features with a precision not previously attainable. Solutions to analytical expressions of the model, as-obtained with appropriate parameter values for a given sculpting process, can be employed in accordance with the invention to produce prespecified nanoscale features in a precise, predictable manner, and in open-loop fashion, i.e., without the need for closed-loop ion counting rate feedback control like that provided by the feedback system of FIG. 3A described above. As explained in detail below, the invention provides a recognition that the ion beam sputtering and mass transport phenomena discussed above compete during an ion beam sculpting process. The methodology of the invention provides the ability to control these phenomena such that one can be made to dominate over the other in a manner to enable production of a desired nanoscale feature or geometry.

The invention provides analytical model expressions that are based on process parameters which generally depend on the properties of a material being ion beam sculpted, e.g., the specific material composition, the initial geometry of a structure or feature at the material surface, material defects, and doping impurities, as well the local environment around the sculpting process, for example the gaseous ambient environment, the temperature of the material, the incident ion species, ion flux, and ion energy, and other parameters that characterize the incident ion beam. It is recognized in accordance with the invention that the process parameters therefore are to be adjusted based on a particular ion beam sculpting application to achieve desired process results, in the manner described below.

For clarity, the following discussion is directed to a process model based specifically on ion beam sculpting of a nanopore of a selected diameter, or area. As explained in detail below, however, the invention is not limited to such. The analytical process model expressions provided by the invention can be adjusted to control formation of a wide range of geometries, e.g., slits or irregularly-shaped holes, trenches, or other geometry, extending through the entire thickness of a material or through only a portion of the thickness. In addition, positive features, rather than negative features such as apertures, can be formed on a material surface or in a material, in the manner previously described. Features such as lithographic mask features, ion beam doping profiles accompanied by mass transport, or buried layer profiles can further be produced in accordance with the process model provided by the invention. Further, the dimensions of existing features can be controlled, or changed, in accordance with the invention. There is no fundamental geometric symmetry or pattern to which the process control model is limited. Whatever geometry or feature is being formed, controlled, and/or changed, it is the nanoscale control of that geometry by the methodology of the invention that is universally applicable.

As explained above, the model employed by the invention for use in controlling ion beam sculpting is based on a recognition that distinct processes are likely to compete during the sculpting. Considering ion beam sculpting of a nanopore to reduce a starting diameter of a pore to a selected reduced diameter, a first such competing process tends to open the pore and is understood to likely be driven by ion beam-sputter erosion of a pore edge. This erosion process is understood to be dominant at low temperatures and high ion beam fluxes. Established sputtering phenomenology can be employed for most applications to account for and control sculpting processes that are dominated by sputtering in this regime.

A second, competing process tends to cause motion of matter, i.e., mass transport, and can operate to a degree necessary for reducing the starting pore diameter. Without being bound to theory, it is understood that more than one view can explain this phenomenon. A first theory understood in accordance with the invention takes the view that a very thin, e.g., about 5 nm-thick, stressed viscous surface layer can be created by the energy and matter deposited on a material surface by an ion beam. An enhanced collective motion, driven by a reduced viscosity and/or enhanced stress owing to implantation effects or surface tension, may cause the layer to flow or relax, whereby material is transported across a surface.

Although this "viscous flow" model has merit, in accordance with the invention a preferred ion beam sculpting control model reflects a process theory in which incident ions create as well as annihilate excess, independent, and mobile species such as adatoms, ad-dimers, ad-molecules, molecular clusters and surface vacancies that are present at the surface of a material exposed to an ion beam. For most applications, it is understood to be reasonable to assume a single mobile species which, for simplicity, will here be called an "adatom." The changing concentration of surface adatoms, C(r,t), is modeled in accordance with the invention as a function of distance, r, along the surface, and time, t, governed by a two dimensional diffusion expression as:

$$\frac{\partial}{\partial t} C(r, t) = FY_1 + D\nabla^2 C - \frac{C}{\tau_{trap}} - FC\sigma_C, \quad (1)$$

where C is the concentration of adatoms on a two-dimensional surface, r=(x,y) is the radial surface position, t is time, F is the ion flux, $Y_1$ is the number of adatoms created per incident ion, D is the adatom surface diffusivity, rap is the average lifetime of an adatom before thermally-activated adatom annihilation occurs at a surface defect, and $\sigma_C$ is the cross-section for adatom annihilation by incident ions.

Figure 13:
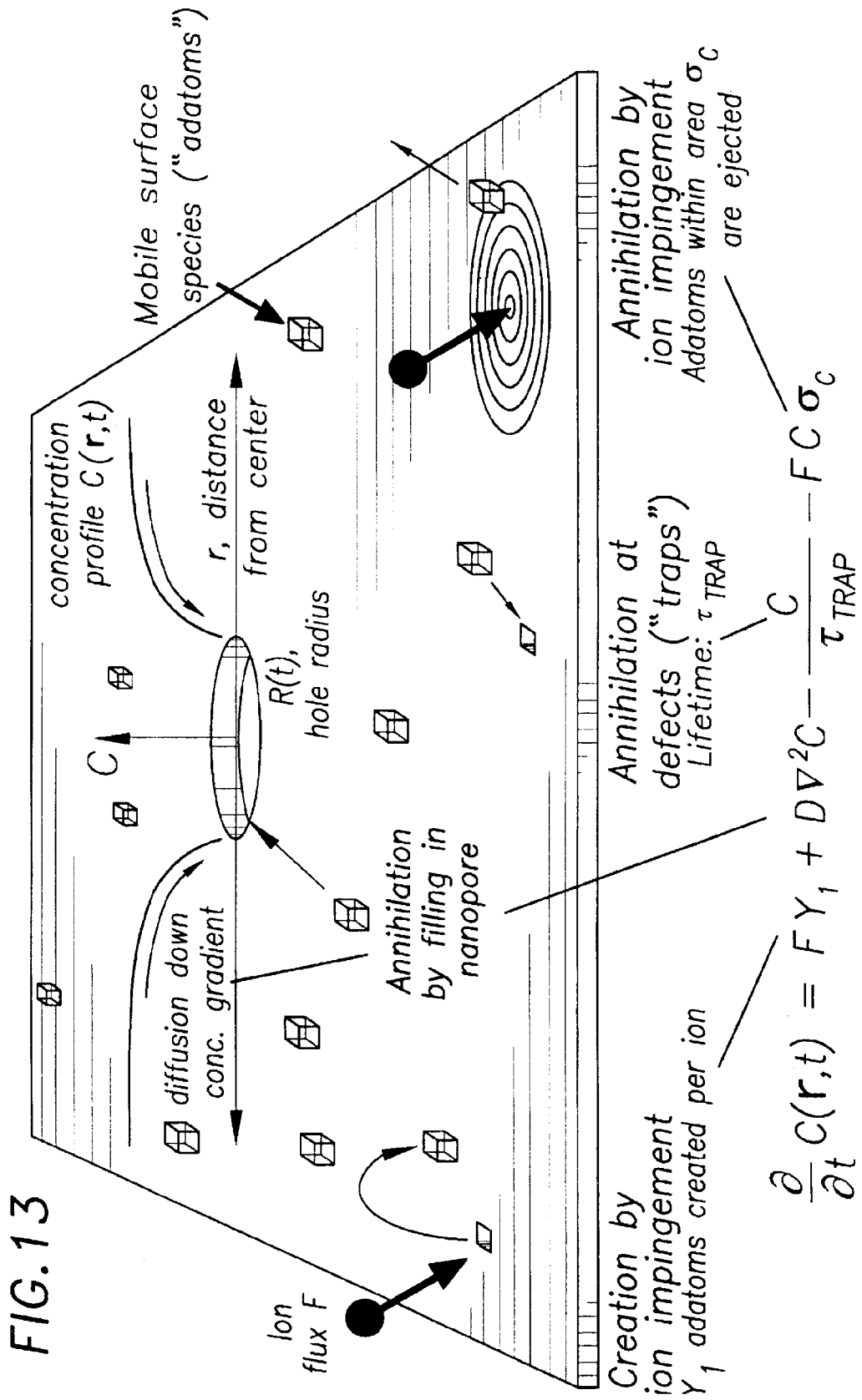
FIG. 13 is a schematic view of a solid state structure surface undergoing a material transport and ion sculpting process provided by the invention, identifying physical mechanisms corresponding to various terms of an ion sculpting model provided by the invention.

FIG. 13 schematically illustrates the competing mechanisms modeled by this expression. Changes in concentration of surface adatoms, $\partial C/\partial t$, depends firstly on a rate of generation of adatoms that results from the ion flux, F, with $Y_1$ indicating the number of created adatoms per incident ion. The second modeled term is a mass transport term, driving the adatom transport by diffusion along the surface and within the structure, and thus depending on the adatom surface diffusivity, D, and the adatom concentration gradient. This transport term models the reduction in a nanopore radius by mass transport of material from around the pore, in the manner described and demonstrated above.

Further as shown in FIG. 13, the surface adatom concentration change is determined by adatom annihilation that can occur at a surface defect, or trap; $\tau_{trap}$ is correspondingly defined as the average lifetime of an adatom before such annihilation at a trap occurs. The final term models ion beam annihilation of adatoms; here $\sigma_C$ reflects the cross-section for adatom annihilation by the incident ion beam itself. It is also understood that annihilation of adatoms occurs at the pore edge as the pore is filled by the mass transport phenomena; this annihilation mechanism is treated as a boundary condition for Expression (1) above.

The first and last terms on the right hand side of Expression (1) above reflect an understanding provided by the invention that each incident ion resets a surface patch of area given as $\sigma_C$ to an adatom concentration given as $Y_1/\sigma_C$ that is independent of its previous state. The presence of a nanopore of an initial diameter in the material being subjected to an ion flux is represented by adding an adatom sink at the nanopore edge, for a nanopore radius, R, and by including the second term on the right hand side of the expression to model long-range material diffusion to the pore edge. Adatoms annihilated at the nanopore boundary are turned into new, stable matter at the boundary.

The magnitudes of the parameters $Y_1$, D, $\tau_{trap}$, and $\sigma_c$ can be estimated for a given ion beam sculpting application from experience with suitable materials and can be determined by independent experiments. For example, a matrix of pore-closing experiments can be conducted, preferably including both steady state and transient conditions, and employing the feedback system of the invention described previously for making precise determination of the influence of each parameter on feature formation, e.g., pore-reduction rate, and other characteristics. One or more "test" ion flux exposures of a material structure can be carried out under a variety of test process conditions, with each "test" exposure monitored by the ion counting feedback loop previously described above. This monitoring enables an indication of feature fabrication dependence on the test process conditions. In turn, the magnitudes of the model parameters, and corresponding optimal process conditions, can then be determined and selected based on the accumulated test process results. It is recognized in accordance with the invention that the values of the model parameters can be manipulated by adjusting not only temperature, ion beam flux, and ion beam energy, but also by adjusting the ambient gas species and pressure, ion species, material properties, e.g., concentrations of trace impurities on the material surface, material defects, and impurity doping. The parameters are therefore treated here as being fully adjustable to enable selection based on test process results, if desired, and to enable precise control of the ion beam sculpting process for a given application.

By comparison with the trapping annihilation term of the right hand side of Expression (1) above, the ion impingement annihilation term of the right hand side of Expression (1) above corresponds to an average adatom lifetime before ion impingement-induced annihilation as $\tau_{ion}=1(F\sigma_C)$. Thus, the effective surface lifetime, $\tau$, of an adatom in the presence of both annihilation mechanisms can be given as:

$$\frac{1}{\tau} = \frac{1}{\tau_{trap}} + F\sigma_C \qquad (2)$$

It is understood that under some circumstances, one of the two annihilation terms of the right hand side of Expression (1) above will be insignificant compared to the other, but this may not necessarily always be the case, and is not required for the analysis of the invention.

An additional annihilation mechanism, namely, adatom annihilation by joining of adatoms and precipitation into adatom islands, is not represented in Expression (1) for simplicity so that this partial differential equation is linear, rather than nonlinear, for ease of analytical mathematical solution. It is understood, however, that applications for which this annihilation channel cannot be neglected are more precisely modeled with the addition of another term to the right hand side of Expression (1) that would be proportional to $-C^n/\tau_{island}$, where n is the number of adatoms in an critical island of a critical size, i.e., a size just large enough to be more likely to grow than to shrink, and $\tau_{island}$ is a characteristic time constant for adatom island formation. Thermal generation of adatoms, thermal desorption of adatoms into a surrounding vacuum, and deposition of adatoms from an ambient vapor are additional mechanisms that have also been neglected for clarity but can be readily incorporated, when necessary for a given application, in the manner of the mechanisms described above.

Expression (1) above expresses an understanding provided by the invention that far from a feature, e.g., a nanopore, steady ion beam irradiation of a material surface creates on the surface and at the near-surface a spatially uniform, steady state adatom concentration $C_{SS}=FY_1\tau$. The pore boundary, or nanopore edge, is taken to be a "perfect sink" for adatoms, which are there transformed to a thin layer of accumulating matter that accounts for pore reduction. If the nanopore edge is taken as a sink for adatoms then the adatom supersaturation drops as the nanopore edge is approached. Expression 1 above implies that the normalized difference, $n(r,t)$, between $C_{SS}$ and $C(r,t)$, given as $n(r,t) \equiv (C_{SS}-C(r,t))/C_{SS}$, obeys a diffusion equation as:

$$\frac{\partial n(r,t)}{\partial t} = D\nabla^2 n - \frac{n}{\tau}. \qquad (3)$$

The assumption that the pore boundary is a "perfect sink" for adatoms implies that the adatom concentration, C, vanishes at the pore boundary, shown as in FIG. 13 to be of radius R. This is the simplest boundary condition that accounts for a net accumulation of adatoms at the pore, and thus for reduction of pore diameter. It is recognized in accordance with the invention, however, that because of its interaction with the ion beam, the pore boundary could be a net source of surface vacancies while producing this pore-reducing effect if vacancies, rather than adatoms, dominate surface transport. The invention is therefore not limited to an adatom "perfect sink" boundary condition. An alternative boundary treatment contemplated by the invention employs a surface accommodation velocity to describe a partial sink for adatoms at the pore boundary, in a manner analogous to surface recombination velocity factors employed in semiconductor modeling of charge carriers interacting with surfaces. These pore boundary conditions can be directly generalized to other feature location characteristics.

The diffusion model employed by the control method of the invention is thus found to be phenomenological in nature, relying on several idealizations and assumptions to compensate for uncertainty in aspects of many microscopic properties of matter under ion beam exposure. Nevertheless, it is understood by the inventors that studies of pulsed and continuous ion beam exposures at different temperatures, gas ambients, and material conditions can be employed for a given application in conjunction with the model to permit the determination of materials-specific parameters like diffusivity, D, ion-induced adatom population $Y_1$, area of adatom annihilation by ion impingement $\sigma$, and adatom lifetime prior to trap annihilation, $\tau_{trap}$, for a given application. Such analysis enables prespecified and precise ion beam sculpting of the material in the production of useful nanoscale devices.

In addition, practitioners of ion beam sculpting can use the model provided by the invention in both quantitative and qualitative ways. That is, by knowing the qualitative as well as quantitative nature of the solutions to the analytical model expressions and their dependence on various parameters of the model that are subject to experimental control, the parameters can be adjusted to achieve desired dimensional control of structures for large classes of structures. For example, the model demonstrates a qualitative dependence of an ability to increase the rate of pore reduction, and even the possibility of reducing a pore diameter at all with ion sculpting, by increasing the material temperature or by decreasing the incident flux of incident ions. The model also provides a quantitative dependence of the precise degree of temperature increase or flux decrease required for a given application. In these examples, practitioners are guided to such action by noting that both of these actions increase the effectiveness of surface diffusion of adatoms over sputtering, by a temperature enhancement of the surface diffusion constant and a reduction in adatom sputtering, respectively.

Other qualitative and quantitative uses of the model include correlations between analytical predictions of the model and ancillary empirical observations. For example, an observation that nanopores, the area of which are reduced to a desired area more quickly under the ion beam sculpting process, may require a minimum initial diameter before the sculpting process can be effective, can be correlated to process conditions via the model. Although the model at any given stage of its solution evolution may not contain the details of the process controlling the pore diameter, it can be used to correlate the process control parameters, and thereby, e.g., control the process mechanisms.

In a further example, consider the reduction in diameter of a nanoscale pore from a starting pore diameter down to a selected final diameter in the manner described above with reference to the pore shown in the electron micrographs of FIGS. 7A–7B. A plot of pore area as a function of ion beam dose, as in FIGS. 9A–9B, demonstrates that for a given ion beam dose, as the incident ion beam flux is reduced, mass transport of material increases, thereby more quickly reducing the diameter of the pore. As explained above, the strong nonlinearity of this result indicates that at high, ion beam fluxes, the mass transport mechanism captured by the model of the invention may become suppressed. Analysis and testing based on the model of the invention enables a correlation of this flux dependence for given material and ion beam characteristics.

Figure 14A:
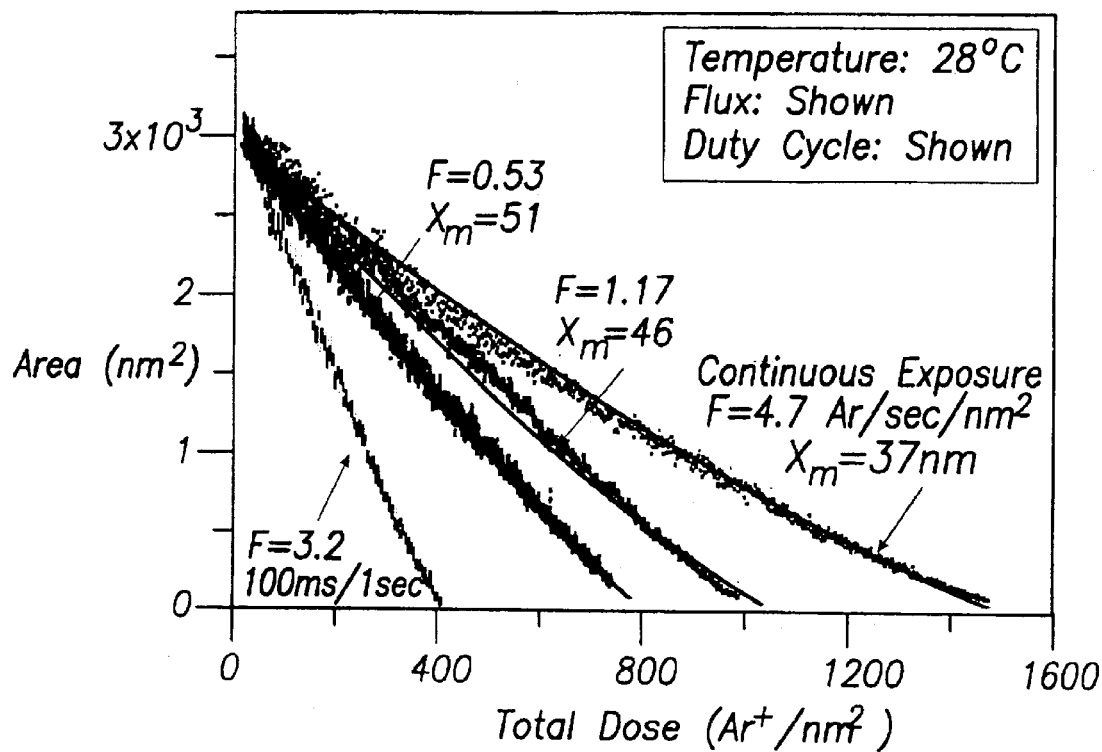
FIG. 14A is a plot of aperture area as a function of total ion dose for four different ion fluxes and for continuous as well as periodic ion flux exposure, for the material transport processes provided by the invention.

FIG. 14A provides a similar plot of pore reduction data, here of nanopore area as a function of total ion beam dose for several ion beam fluxes and for continuous as well as pulsed ion beam exposure. The dotted plot points correspond to experimentally measured results, and the solid lines correspond to results produced by analysis of Expression (1) above, as explained in detail below. The slope of this data demonstrates that for continuous ion beam exposure, where the ion beam flux, F=0.53, 1.17, and 4.7 Ar/sec/nm$^2$, the efficiency of pore closing per incident ion is clearly greater at low fluxes than at high fluxes. This plotted data also demonstrates that pulsed ion beam exposure, here at 100 ms/1 s, provides more effective mass transport, and a correspondingly increased rate in pore area reduction, than does a continuous ion beam at the same instantaneous flux. Particular control methodology provided by the invention for the plotted pulsed ion beam exposure data is described below.

Thus, as explained above, in accordance with the invention, ion beam sculpting process parameters can be adjusted for a given application, based on the process model provided by the invention, to enable prescription of nanoscale geometries produced by the sculpting process. As explained above, parameters will in general depend on the composition of the material being ion sculpted, the environment around the structure during the sculpting process, temperature, and on the incident ion species, energy, and other parameters that characterize the incident ion beam. The incident ion beam can be supplied as atoms, i.e., neutral ions, ions of a controlled charge state, molecules or clusters of incident atoms, or indeed any controlled energy source. It is recognized that differing model parameters will be required for various energy sources. In addition, the invention contemplates the use of multiple energy sources as well as adjustment of the charge state of the material surface at the start and during the sculpting process.

It is recognized in accordance with the invention that both the surface of a structure being ion sculpted and the ion-induced adatoms on the surface may be highly susceptible to the influence of the environment. By environment is meant a background ambient of a gas like oxygen, hydrogen, sulfur hexafluoride, or other selected gas. As a result the interaction of these gasses with surface atoms and/or adatoms, the transport of adatoms and/or the removal of surface atoms and adatoms can be greatly modified, relative to a process carried out in the absence of such gasses. Consequently, the rates and signs of ion sculpting mechanisms captured in the model provided by the invention will be dramatically modified by ambient gas species, and these modifications can be of great utility for precise control of the ion beam sculpting process.

It is also to be recognized that the state and chemical reactivity of the ambient gas, as well as the excitation state of the surface or charge state of the surface being acted upon, can be influenced by, or catalyzed by, the incident ion beam. This can result in removal or addition of adatoms and/or creation or elimination of surface defect traps, thereby influencing the mass transport and annihilation mechanisms of the ion sculpting process. Means other than an incident ion beam, such as an electron beam, laser beam, atomic beam, metastable excited atomic beam, mixtures of ion beams, or other energy source, can be used to control the sensitivity of the ion sculpting process to the ambient environment in which the process is carried out. Adjustment and control of these various influences are recognized in accordance with the invention to enable flexibility and reproducibility of prespecified and precise ion beam sculpted geometries of a material in the production of useful nanoscale devices.

As mentioned above, the charge state of an ion beam can be adjusted based on a particular ion beam sculpting application to achieve desired ion sculpting process results. Positive, neutral, or negative ions can be employed in accordance with the invention to produce a desired surface force between adatoms that are produced and transported along the surface during the sculpting process.

Turning to more quantitative solutions of the analytical model provided by the invention, and referring back to Expression (1) above, it is clear that the ion sculpting process can be specifically controlled by controlling the dominance of adatom creation and transport mechanisms relative to adatom annihilation mechanisms. Specifically, the adatom creation mechanism, represented by the term $FY_1$, along with the adatom mass transport mechanism, represented by the term $D\nabla^2 C$, can be controlled to dominate, or alternatively be dominated by, the adatom trapping annihilation mechanism, represented by the term C/$\tau_{trap}$, together with the adatom ion impingement annihilation mechanism, represented by the term FCσ$_C$. This control accordingly enables a "starting" and "stopping" of an ion sculpting process to achieve a desired feature geometry.

Specifically, in accordance with the invention, process parameters that influence the ion flux, F, and adatom diffusivity, D, are selected relative to process parameters that influence surface defects and ion impingement characteristics, to control the adatom concentration and transport. For example, material temperature, material surface conditions, and other material dependent characteristics can be selected to increase adatom diffusivity, D, thereby to enhance mass transport to a feature being ion sculpted and to maximize the rate at which an ion sculpted feature is produced. Minimization of surface defects and other material trapping mechanisms can be carried out to minimize annihilation of adatoms by traps, thereby further enhancing the mass transport mechanism of the ion sculpting process.

Considering the influence of the ion beam flux, F, as explained above with reference to the plot of FIG. 14A, as ion beam flux is increased, adatom annihilation by ion impingement also increases, resulting in a reduction of adatom concentration and transport to a feature to be produced. But at the same time, as ion beam flux is increased, the number of adatoms created also increases. Ion beam flux is therefore preferably controlled to influence adatom creation and adatom annihilation, thereby to determine the availability of adatoms for the ion sculpting process. Control of incident ion species and energy, and control of the gaseous process ambient enable control of the factors Y$_1$ and σ$_C$ similarly to control adatom creation and annihilation.

Specific solutions for the spatial adatom concentration profile given by the model in Expression (1) can be achieved under a quasi-stationary approximation in which the left hand side of Expression (1) is set to zero. This scenario is justified for applications in which the adatom concentration profile of a material being processed adjusts rapidly to changes in feature geometry, e.g., changing pore radius, R, and ion flux, F. With this assumption, the model yields a spatially uniform steady-state adatom supersaturation concentration far from the pore edge, decaying over a characteristic mass transport distance, X$_m$, to zero at the nanopore edge.

Because adatoms are being removed everywhere on the surface of a material exposed to ion beam irradiation, as well as being created by the ion beam, adatoms created within the mass transport distance, X$_m$, of a feature, e.g., a pore edge, are more likely to diffuse to and add to the material at the pore edge than be annihilated by incident ions; the opposite is true of adatoms created farther away. The mass transport distance, X$_m$, therefore decreases with increasing flux.

Obtaining Y$_p$, the effective cross section for sputter-erosion from the pore edge, from relevant data obtained at low temperature, where diffusion is expected to be insignificant, and taking Y$_1$, the number of adatoms created per incident ion, to be of order unity, then for a material thickness of about 10 nm for a silicon nitride sample, the model of Expression (1) yields the solid curves of the plots of FIG. 14A for each Argon flux given, at a temperature of about 28° C., which is a temperature experimentally verified to cause pores to be reduced.

Figure 14B:
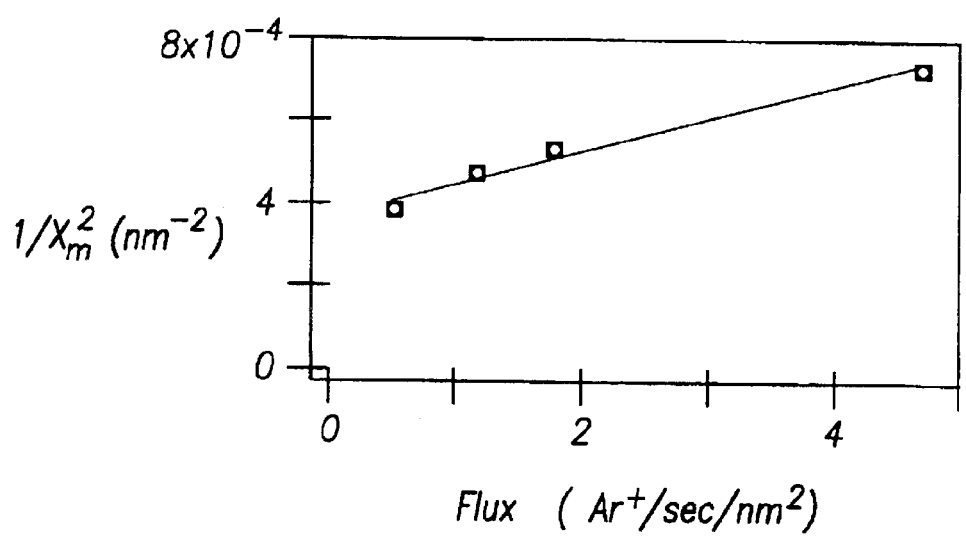
FIG. 14B is a plot of the inverse of adatom diffusion distance as a function of incident argon ion flux.

From this data, a value of diffusivity, D, of about $10^3$ nm$^2$s$^{-1}$ is extracted, using a linear fit, with σ$_C$ of about 0.1 nm$^2$ as a reasonable estimate. From this experimental data, it is found that the model therefore predicts that the maximum distance, X$_m$, from which adatoms are likely to diffuse to and add to material at a feature location, e.g., at the edge of a reducing pore, is linearly proportional to the adatom diffusivity, the trap lifetime, the ion beam flux, and the cross section for adatom annihilation, as:

$$\frac{1}{X_m^2} = \frac{1}{D\tau_{trap}} + \frac{\sigma_C}{D}F \qquad (4)$$

and a linear relation is indeed observed, as demonstrated by the plotted data of FIG. 14B. FIG. 14A provides an indication of the corresponding mass transport distance, X$_m$, for each ion flux considered. The mass transport distance, X$_m$, thus is found to represent a characteristic distance from the pore edge within which adatoms are more likely to reach the pore than be annihilated by traps or ion beam flux erosion. Adatoms beyond a distance X$_m$ from a feature to be formed, such as a pore edge, are more likely to be annihilated before they reach the pore edge.

Considering particular parameter effects, as the ion beam flux is increased, the number of produced adatoms is increased, but the distance from which adatoms can diffuse to and add to a pore edge is reduced. As the average lifetime of an adatom is increased by a reduction in surface defects, the maximum adatom diffusion distance also increases. As the temperature is increased, the diffusivity, and correspondingly, the maximum adatom diffusion distance, is increased. With the analytical understanding of these relationships provided by the invention, the model thereby enables an ability to prescribe a minimum distance, X$_m$, of material that must be provided around a starting feature, such as a nanopore, or around a location at which a feature is to be fabricated, to provide sufficient material for fully forming the feature, e.g., for reducing the radius of the nanopore to a desired final radius, R, under given processing conditions, and enables adjustment of processing conditions to accommodate a maximum diffusion distance X$_m$ that is available for a given application.

The adatom flux, or current, j, at any location, r, of a surface being processed is given by $$j(r) = -D\ \partial C/\partial r, \qquad (5)$$

with r the radial coordinate, and the concentration gradient evaluated at the edge of the nanopore, at r=R, providing an indication of the adatom flux j(R) to the edge of the nanopore material. Additionally, scraping of material off the edge of the nanopore, tending to increase the pore area, is accounted for by a characteristic cross section for sputter-erosion from the pore edge.

If each adatom reaching the nanopore fills the pore by a volume Ω, thereby reducing the extent of the pore, then the nanopore reduction rate is predicted by a volume balance given as:

$$\frac{d}{dt}(\pi R^2 H) = 2\pi R\Omega(-j(R) + FY_p), \qquad (6)$$

where Y$_p$ is an effective cross section for sputter-erosion from the pore edge, H is the thickness of a film that is formed as the nanopore is reduced, or filled in, and Ω is the atomic volume. Substituting Expression (5) above for the adatom current j(R) at the edge of the nanopore results in:

$$\frac{d}{dt}(\pi R^2) = -\frac{2\pi\Omega RF}{H}\left(Y_1 X_m \frac{K_1\left(\frac{R}{X_m}\right)}{K_0\left(\frac{R}{X_m}\right)} - Y_p\right), \quad (7)$$

where $K_0$ and $K_1$ are modified Bessel functions of the second kind.

This expression enables ion beam sculpting control, for a given set of process parameters characteristic of an ion beam environment, to produce a nanopore of a desired radius R. For example, it is found from this model that reduction of pore radius is enhanced with increasing temperature. This can be accounted for by a thermally activated adatom diffusion coefficient in the manner described above.

Based on this understanding, if the process parameters that influence adatom creation and mass transport are selected such that the first two terms of the right hand side of Expression (1) above dominate the second two terms of the right hand side of Expression (1), then ion sculpting to form a selected feature in a material being ion-irradiated proceeds. On the other hand, if the process parameters that influence adatom annihilation by traps and adatom annihilation by ion impingement are selected such that the second two terms of the right hand side of the Expression (1) dominate, then material sputtering and removal, rather than mass transport of the material from one surface location to another, is controlled to occur.

Thus, in accordance with the control method of the invention, with this methodology, Expression (7) can be employed to specify $R_{max}$, the largest starting pore radius that can be reduced at all under any particular set of processing conditions. This maximum starting radius, $R_{max}$, increases with increasing temperature and with decreasing ion beam flux. At a sufficiently high temperature and sufficiently low ion beam flux, $R_{max}$ becomes infinite, in a scenario that determines the conditions under which an open pore can be closed. The maximum radius, $R_{max}$ is thus given by:

$$Y_1 X_m \frac{K_1\left(\frac{R_{max}}{X_m}\right)}{K_0\left(\frac{R_{max}}{X_m}\right)} - Y_p = 0. \quad (8)$$

With $X_m$, $Y_1$, and $Y_p$ provided as constants, the ratio of $$\frac{K_1\left(\frac{R}{X_m}\right)}{K_0\left(\frac{R}{X_m}\right)}$$

gets smaller with increasing pore radius, R, so that at $R=R_{max}$ and above, the pore radius cannot be reduced. Analysis of this expression thereby enables adjustment of processing conditions to produce a desired $R_{max}$ or to accommodate a maximum radius, $R_{max}$, that is fixed by a given application.

It has been observed empirically that the thickness, H, of a growing membrane or film produced as a nanopore radius is reduced and a pore is filled in depends on the rate of reduction, $d(\pi R^2)/dt$, where R is the radius of the nanopore. Higher pore reduction rates result in thinner films than lower pore reduction rates. In addition, higher ion beam energies result in thicker films than lower ion beam energies. Based on the expressions given above, the invention provides the ability to prescribe a selected film thickness by selecting ion beam sculpting process conditions, and particularly ion beam energy, that result in a desired pore reduction rate and film thickness.

As explained above, it is understood in general in accordance with the invention that different regions of the perimeter of an arbitrarily-shaped aperture will also open and close according to Expressions 1–4 above. In addition, Expressions 4–8 above can be generalized in an obvious manner to remove the cylindrical symmetry assumed in the example given here, to enable modeling and process control of arbitrarily-shaped features. Thus, as stated above, the invention is therefore not limited to a particular feature geometry.

Time dependent solutions of the adatom diffusion model can be employed in accordance with the invention to describe an ion sculpting process employing a pulsed ion beam having a selected duty cycle. In order to model conditions when the incident ion beam is turned off, a steady state condition is assumed for the initial concentration profile. That is, the ion beam flux is set to F=0, and the initial concentration of the adatoms on the surface is given, for the nanopore example above, as:

$$C(r, t = 0) = C_{ss}\left[1 - \frac{K_0\left(\frac{r}{X_m}\right)}{K_0\left(\frac{R}{X_m}\right)}\right], \quad (9)$$

where $C_{SS}$ is the steady state adatom concentration far from the pore edge. Substitution of this initial concentration into Expression (1) above then provides:

$$\frac{\partial}{\partial t}C(r, t) = D\nabla^2 C - \frac{C}{\tau_{trap}}, \quad (10)$$

with assumed boundary conditions for the adatom concentration, C, as:

$$C(R, t) = 0 \quad (11)$$
$$C(b = NX_m, t) = C_{ss}e^{-\frac{t}{\tau_{Trap}}},$$

where b is an outer boundary condition, far from the pore edge, i.e., N>>1. In practical calculations, N=5 is typically sufficiently large, but it is recognized that for some applications, a larger value of N can be required for increased accuracy.

Solutions to Expression (10) above provide time dependent solutions of the adatom concentration on the surface of a material being processed after the beam is off, as:

$$C^{off}(r, t) = C_{ss}\left[\frac{\ln\left(\frac{r}{R}\right)}{\ln\left(\frac{b}{R}\right)} + \sum_{n=1}^{\infty} A_n U_0(\alpha_n r)e^{-\alpha_n^2 Dt}\right]e^{-\frac{1}{\tau_{Trap}}}, \quad (12)$$

where $$A_n = \frac{\pi^2 \alpha_n^2}{2} \frac{J_0^2(\alpha_n R)}{J_0^2(\alpha_n R) - J_0^2(\alpha_n b)} \int_R^b r\left[1 - \frac{K_0\left(\frac{r}{X_m}\right)}{K_0\left(\frac{R}{X_m}\right)} - \frac{\ln\left(\frac{r}{R}\right)}{\ln\left(\frac{b}{R}\right)}\right]U_0(\alpha_n r)dr.$$

Given: $U_0(\alpha r) = J_0(\alpha r)Y_0(\alpha b) - J_0(\alpha b)Y_0(\alpha r)$
and $U_0(\alpha_n R) = J_0(\alpha_n R)Y_0(\alpha_n b) - J_0(\alpha_n b)Y_0(\alpha_n R) = 0$, to provide the roots of $\tau_n$. $J_0$ and $Y_0$ are Bessel functions of the first kind.

The rate at which the area of a pore decreases when the ion beam is off, or the material is not being irradiated by the beam, is given as:

$$\left(\frac{\partial}{\partial t}(\pi R^2) = -\frac{2\pi \Omega R}{H} D \frac{\partial C^{off}}{\partial r}\Big|_{r=R}\right) \quad (13)$$

When a material being processed is not irradiated by the ion beam, i.e., just after the beam is extinguished or the material is shielded from the beam, mobile adatoms remain on the surface of the material, but the adatom annihilation mechanism associated with the incident beam flux is no longer present. Thus, once the material is not exposed to the ion beam, those adatoms remaining on the material surface can diffuse to the pore periphery from a greatly increased $X_m$. This condition is discovered to significantly increase the efficiency per ion for pore radius reduction. Indeed, as shown in the plot of FIG. 14A, a pulsed ion beam irradiation process is found experimentally to be more efficient in forming a feature, here in reducing the radius of a pore, than continuous exposure conditions.

In accordance with the invention, Expression (13) can be employed in combination with Expression (7) above to predict and then control the rate of feature formation or change, e.g., nanopore diameter reduction, when a pulsed ion beam sculpting process is employed. Specifically, the pulsed ion beam time structure, i.e., the pulse rate and duty cycle, can be adjusted in accordance with the invention to achieve control over the sign and rate of change of structural dimensions.

It is recognized in accordance with the invention that as with the conditions when the beam is turned off, there is also a transient solution when the beam is first turned back on or the structure is again exposed to the beam. This transient may be important under some conditions, but it is understood that for most applications, the "beam-on" transient is significantly shorter than the "beam-off" transient and therefore can be ignored. If for a given application such is not the case, then the "beam-off" transient analysis given above is preferably extended to the "beam-on" analysis. Then the duty cycle of the ion beam irradiation can be particularly selected to achieve desired ion sculpting results.

To demonstrate the effectiveness of the process control methodology of the invention, a nanopore was sculpted in a $Si_3N_4$ membrane for use as a single-molecule electronic detector of DNA. Proteinaceous nanopores, or channels, have been inserted into lipid bilayers in aqueous solutions where they serve as electronic sensors to identify and characterize single molecules. But proteins in lipid bilayers are labile and the channel diameters they provide cannot easily be adjusted. Robust, solid-state nanopores provided in accordance with the invention, fashioned to any desired diameter, enable a yield of new data and understanding of transport in confined spaces, and make it possible to produce robust single-molecule-sensing devices to characterize molecules of DNA and other biopolymers at unprecedented speeds.

Figure 15:
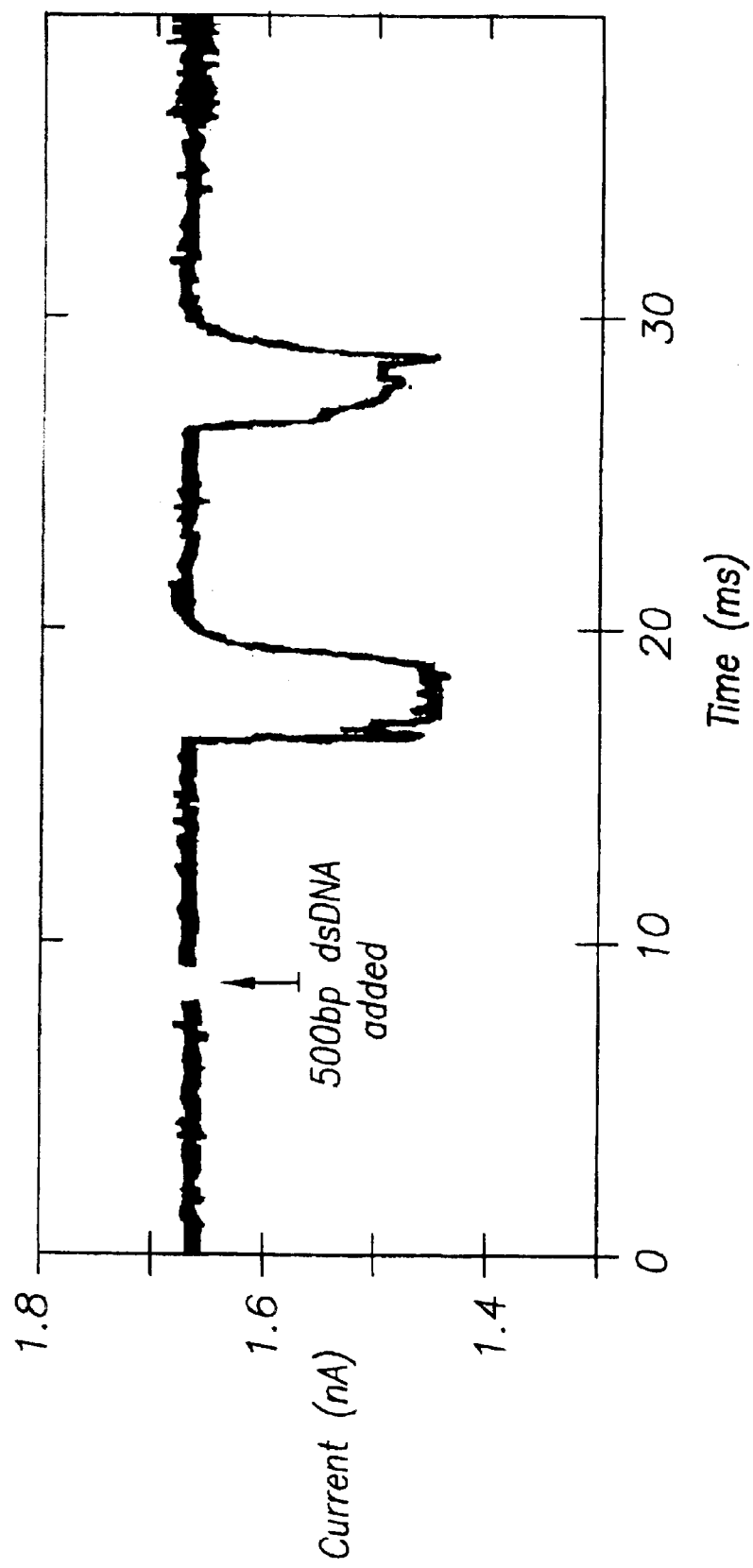
FIG. 15 is a plot of measured current as a function of time produced as negatively charged DNA molecules were drawn through a nanopore produced in accordance with the invention in a silicon nitride membrane.

A 5 nm-diameter pore in a silicon nitride membrane was produced in accordance with the process parameters and process control described above. Then, using electrophysiology techniques, the pore was tested with double-stranded DNA. After applying a voltage bias that would draw the negatively charged DNA molecules through the nanopore, diminutions of the ionic current were observed, as shown in FIG. 15, in a manner analogous with the ionic-current blockages observed when single strands of DNA are translocated through the channel formed by α-hemolysin in a lipid bilayer. Because no such reductions in current were observed during one hour of monitoring before adding DNA, and because the reductions in current ceased to occur when the voltage bias was reversed, the reductions in current are attributed to interactions of individual DNA molecules with the nanopore. The duration of these reductions in current was found to be on the order of milliseconds, and to consistently fall to a current value of about 88% of the open-pore current value. This last value is commensurate with translocation of a rod-like molecule whose cross-sectional area is 3–4 $nm^2$.

The experimental observations, model considerations and control methodology, and experimental electronic device results all described above indicate that the ion beam-sculpting control method of the invention represents a superior approach to nanoscale fabrication. Specifically, the invention enables control of sputtering and mass transport processes that compete during an ion beam sculpting process. With the feedback control techniques described above, reproducibility does not depend on precisely matching all conditions and starting dimensions. If, however, such can be achieved, then the control model of the invention enables open loop processing without reliance on ion rate counting or other feedback control. The invention therefore is not limited to features or geometries that can accommodate an ion counting feedback loop.

The ion beam-sculpting control method of the invention is particularly useful for fabricating a wide variety of nanoscale semiconductor devices, masks, and mechanical features, and as explained above is not limited to formation of a pore or a through-hole. Slits, trenches, crosses, doping profiles, resist patterning, buried layer profiles, and other geometries and features can be produced and dimensionally controlled, or changed. Similarly, a wide range of materials can be employed, including microelectronic materials such as Si, $SiO_2$, $Si_3N_4$, Al, and a wide range of others. Furthermore, it is recognized that next-generation ion-source arrays and mask technologies, combined with multichannel ion detectors, can be employed to enable highly parallel applications of the nanoscale ion beam sculpting control methods of the invention.

This discussion highlights the wide range of applications of the solid state feature formation and dimensional control processes of the invention. The subtractive and additive materials processing techniques of the invention, in conjunction with the physical species detection and feedback control of the invention, enable reproducible and highly precise feature formation. The advantages of this precision and control are most apparent when applied to nanometric feature dimensions and dimensional tolerances. It is recognized, of course, that those skilled in the art may make various modifications and additions to the processes of the invention without departing from the spirit and scope of the present contribution to the art. Accordingly, it is to be understood that the protection sought to be afforded hereby should be deemed to extend to the subject matter of the claims and all equivalents thereof fairly within the scope of the invention.

We claim:

1. A method for fabricating a feature of a solid state structure comprising the steps of:

providing a solid state structure having a surface; and exposing the structure to a flux, F, of incident ions, with incident ion exposure conditions being selected based on:

$$\frac{\partial}{\partial t}C(r,t) = FY_1 + D\nabla^2 C - \frac{C}{\tau_{trap}} - FC\sigma_C,$$

where C is concentration of mobile adatoms at the structure surface, r is surface position, t is time, $Y_1$ is number of surface adatoms created per incident ion, D is surface adatom diffusivity, $\tau_{trap}$ is average lifetime of a surface adatom before adatom annihilation occurs at a structure surface defect characteristic of material of the solid state structure, and $\sigma_c$ is a cross-section for surface adatom annihilation by incident ions that is characteristic of the selected ion exposure conditions; to control sputtering of the structure surface by the incident ions and to transport, within the structure including the structure surface, material of the structure to a selected feature location, in response to the ion flux exposure, to produce the feature substantially by locally adding material of the structure to the feature location.

2. The feature fabrication method of claim 1 wherein selection of ion exposure conditions comprises selection of incident ion energy.

3. The feature fabrication method of claim 1 wherein selection of ion exposure conditions comprises selection of incident ion species.

4. The feature fabrication method of claim 1 wherein selection of ion exposure conditions comprises selection of incident ion flux, F.

5. The feature fabrication method of claim 1 wherein selection of ion exposure conditions comprises selection of electronic charge state of the incident ions.

6. The feature fabrication method of claim 1 wherein selection of ion exposure conditions comprises selection of ambient gas species.

7. The feature fabrication method of claim 1 wherein selection of ion exposure conditions comprises selection of ambient gas pressure.

8. The feature fabrication method of claim 1 wherein selection of ion exposure conditions comprises selection of solid state structure material composition.

9. The feature fabrication method of claim 1 wherein selection of ion exposure conditions comprises selection of solid state structure material temperature.

10. The feature fabrication method of claim 1 wherein selection of ion exposure conditions comprises selection of electronic doping of the solid state structure material.

11. The feature fabrication method of claim 1 wherein selection of ion exposure conditions comprises selection of electronic charge state of the solid state structure surface.

12. The feature fabrication method of claim 1 wherein selection of ion exposure conditions is based on solid state structure material surface defect characteristics.

13. The feature fabrication method of claim 1 wherein selection of ion exposure conditions comprises:

carrying out at least one test incident ion exposure of the solid state structure material under selected test incident ion exposure conditions;

directing a physical detection species toward a designated structure location during each test incident ion exposure;

detecting the detection species in a trajectory from the designated structure location to indicate feature fabrication dependence on the test ion exposure conditions; and selecting the ion exposure conditions based on the test ion exposure conditions and the corresponding indicated feature fabrication dependence on the test ion exposure conditions.

14. The feature fabrication method of claim 1 wherein the solid state structure includes an edge boundary location and wherein, the selected feature location comprises a relocated edge boundary location fabricated by the ion flux exposure.

15. The feature fabrication method of claim 14 wherein the solid state structure comprises an aperture having an edge and wherein the relocated edge boundary location comprises a relocated aperture edge fabricated by the ion flux exposure.

16. A method for controlling a dimension of a feature of a solid state structure comprising the steps of:

providing a solid state structure having a surface and having a feature; and exposing the structure to a flux, F, of incident ions, with incident ion exposure conditions being selected based on:

$$\frac{\partial}{\partial t}C(r,t) = FY_1 + D\nabla^2 C - \frac{C}{\tau_{trap}} - FC\sigma_C,$$

where C is concentration of mobile adatoms at the structure surface, r is surface position, t is time, $Y_1$ is number of surface adatoms created per incident ion, D is surface adatom diffusivity, $\tau_{trap}$ is average lifetime of a surface adatom before adatom annihilation occurs at a structure surface defect characteristic of material of the solid state structure, and $\sigma_C$ is a cross-section for surface adatom annihilation by incident ions that is characteristic of the selected ion exposure conditions; to control sputtering of the structure surface by the incident ions and to transport, within the structure including the structure surface, material of the structure to the feature, in response to the ion flux exposure, to change at least one dimension of the feature substantially by locally adding material of the structure to the feature.

17. A method for fabricating a feature of a solid state structure comprising the steps of:

providing a solid state structure having a surface;

exposing the structure to a selected flux, F, of incident ions with incident ion exposure conditions being selected based on:

$$\frac{1}{X_m^2} = \frac{1}{D\tau_{trap}} + \frac{\sigma_C}{D}F,$$

where D is adatom diffusivity at the structure surface, $\tau_{trap}$ is average lifetime of a surface adatom before adatom annihilation occurs at a surface defect characteristic of material of the solid state structure, and $\sigma_C$ is a cross-section for surface adatom annihilation by incident ions characteristic of the selected ion exposure conditions; to control sputtering of the structure surface by the incident ions and to transport, within the structure including the structure surface, material of the structure within a radial distance, $X_m$, to the selected feature location, in response to the ion flux exposure, to produce the feature substantially by locally adding material of the structure to the feature location.

18. The feature fabrication method of claim 17 wherein solid state structure ion exposure is continued for a time sufficient to produce the fabricated structural feature at a location radius, R, given based on the radial distance, $X_m$, as:

$$\frac{d}{dt}(\pi R^2) = -\frac{2\pi \Omega RF}{H}\left(Y_1 X_m \frac{K_1\left(\frac{R}{X_m}\right)}{K_0\left(\frac{R}{X_m}\right)} - Y_p\right),$$

where $\Omega$ is atomic material volume added at the selected feature location by mass transport of an adatom of the solid state structure, H is thickness of structure material transported to the selected feature location, $Y_1$ is number of surface adatoms created per incident ion, $K_0$ and $K_1$ are modified Bessel functions of the second kind, and $Y_p$ is an effective cross section for sputter-erosion of solid state structure material from the selected feature location.

19. The fabrication method of claim 18 wherein the selected feature location radius, R, corresponds to an edge of an aperture in the structure, where H is the thickness of structure material transported to the aperture edge, and where $Y_p$, is an effective cross section for sputter-erosion of solid state structure material from the aperture edge.

20. The fabrication method of claim 18 wherein the selected feature location radius, R, is less than an initial maximum radius, $R_{max}$, given by:

$$Y_1 X_m \frac{K_1\left(\frac{R_{max}}{X_m}\right)}{K_0\left(\frac{R_{max}}{X_m}\right)} - Y_p = 0.$$

21. The fabrication method of claim 20 wherein the initial maximum radius, $R_{max}$, is an initial radius of an aperture in the solid state structure and wherein the selected feature location radius, R, is a reduced aperture radius.

22. The fabrication method of claim 18 wherein ion exposure of the structure comprises exposure of the structure to a flux of incident ions having a characteristic duty cycle of intermittent ion exposure periods separated by non-exposure periods, duration of exposure and non-exposure periods selected to produce the fabricated structural feature at the selected feature location radius, R, based on the radial distance, $X_m$, and based on:

$$\left(\frac{\partial}{\partial t}(\pi R^2) = -\frac{2\pi \Omega R}{H} D \frac{\partial C^{eff}}{\partial r}\right)\bigg|_{r=R}$$

where adatom concentration during non-exposure periods, $C^{eff}$, is given by:

$$C^{eff}(r,t) = C_{ss}\left[\frac{\ln\left(\frac{r}{R}\right)}{\ln\left(\frac{b}{R}\right)} + \sum_{n=1}^{\infty} A_n U_0(\alpha_n r) e^{-\alpha_n^2 Dt}\right] e^{\frac{1}{\tau_{Trap}}},$$

where r is surface position, t is time, $C_{ss}$ is steady state adatom concentration far from the selected feature location radius, b is a selected outer boundary condition, far from the selected feature location radius, and where $$A_n = \frac{\pi^2 \alpha_n^2}{2} \frac{J_0^2(\alpha_n R)}{J_0^2(\alpha_n R) - J_0^2(\alpha_n b)} \int_R^b r\left[1 - \frac{K_0\left(\frac{r}{X_m}\right)}{K_0\left(\frac{R}{X_m}\right)} - \frac{\ln\left(\frac{r}{R}\right)}{\ln\left(\frac{b}{R}\right)}\right] U_0(\alpha_n r) dr, \text{ and}$$

given: $U_0(\alpha r) = J_0(\alpha r) Y_0(\alpha b) - J_0(\alpha b) Y_0(\alpha r)$ and $U_0(\alpha_n R) = J_0(\alpha_n R) Y_0(\alpha_n b) - J_0(\alpha_n b) Y_0(\alpha_n R) = 0$, where $U_0(\alpha r)$ and $U_0(\alpha_n r)$ provide roots of $a_n$, $K_0$ is a modified Bessel function of the second kind, and $J_0$ and $Y_0$ are Bessel functions of the first kind.

* * * * *